(12) United States Patent
Wham et al.

(10) Patent No.: US 7,364,577 B2
(45) Date of Patent: *Apr. 29, 2008

(54) VESSEL SEALING SYSTEM

(75) Inventors: Robert H. Wham, Boulder, CO (US);
Steven P. Buysse, Longmont, CO (US);
James H. Orszulak, Nederland, CO (US)

(73) Assignee: Sherwood Services AG, Schaffhausen (CH)

( * ) Notice: Subject to any disclaimer, the term of this patent is extended or adjusted under 35 U.S.C. 154(b) by 346 days.

This patent is subject to a terminal disclaimer.

(21) Appl. No.: 10/626,390

(22) Filed: Jul. 24, 2003

(65) Prior Publication Data

US 2004/0193148 A1 Sep. 30, 2004

Related U.S. Application Data

(63) Continuation-in-part of application No. 10/073,761, filed on Feb. 11, 2002, now Pat. No. 6,796,981.

(51) Int. Cl.
*A61B 18/18* (2006.01)
(52) U.S. Cl. .......................... 606/34; 606/42
(58) Field of Classification Search ............ 606/32–35, 606/38–42
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |

(Continued)

FOREIGN PATENT DOCUMENTS

DE 179607 3/1905

(Continued)

OTHER PUBLICATIONS

Vallfors and Bergdahl, "Automatically Controlled Bipolar Electrocoagulation" Neurosurgical Review, 7:2-3, pp. 187-190. 1984.

(Continued)

*Primary Examiner*—Michael Peffley

(57) ABSTRACT

A method for electrosurgically sealing a tissue includes steps of: (A) applying a first pulse of RF energy to the tissue; and (B) applying at least one subsequent RF energy pulse to the tissue and keeping constant or varying RF energy parameters of individual pulses of subsequent RF energy pulses in accordance with at least one characteristic of an electrical transient that occurs during the individual RF energy pulses. The method terminates the generation of the at least one subsequent RF pulse upon a determination that the electrical transient is absent.

15 Claims, 17 Drawing Sheets

U.S. PATENT DOCUMENTS

| | | |
|---|---|---|
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,788,634 A | 11/1988 | Schlecht et al. |
| 4,805,621 A | 2/1989 | Heinze et al. |
| 4,818,954 A | 4/1989 | Flachenecker et al. |
| 4,827,911 A | 5/1989 | Broadwin et al. |
| 4,827,927 A | 5/1989 | Newton |
| 4,832,024 A | 5/1989 | Boussignac et al. |
| 4,848,335 A | 7/1989 | Manes |
| 4,848,355 A | 7/1989 | Nakamura et al. |
| 4,860,745 A | 8/1989 | Farin et al. |
| 4,862,889 A | 9/1989 | Feucht |

| | | | | | |
|---|---|---|---|---|---|
| 4,880,719 A | 11/1989 | Murofushi et al. | 5,422,567 A | 6/1995 | Matsunaga |
| 4,890,610 A | 1/1990 | Kirwan et al. | 5,423,808 A | 6/1995 | Edwards et al. |
| 4,903,696 A | 2/1990 | Stasz et al. | 5,423,809 A | 6/1995 | Klicek |
| 4,907,589 A | 3/1990 | Cosman | 5,423,810 A | 6/1995 | Goble et al. |
| 4,922,210 A | 5/1990 | Flachenecker et al. | 5,430,434 A | 7/1995 | Lederer et al. |
| 4,931,047 A | 6/1990 | Broadwin et al. | 5,432,459 A | 7/1995 | Thompson |
| 4,931,717 A | 6/1990 | Gray et al. | 5,433,739 A | 7/1995 | Sluijter et al. |
| 4,938,761 A | 7/1990 | Ensslin | 5,434,398 A | 7/1995 | Goldberg |
| 4,942,313 A | 7/1990 | Kinzel | 5,436,566 A | 7/1995 | Thompson |
| 4,961,047 A | 10/1990 | Carder | 5,438,302 A | 8/1995 | Goble |
| 4,961,435 A | 10/1990 | Kitagawa et al. | 5,443,463 A | 8/1995 | Stern et al. |
| 4,966,597 A | 10/1990 | Cosman | 5,445,635 A | 8/1995 | Denen |
| RE33,420 E | 11/1990 | Sussman | 5,451,224 A | 9/1995 | Goble et al. |
| 4,969,885 A | 11/1990 | Farin | 5,458,597 A | 10/1995 | Edwards et al. |
| 4,993,430 A | 2/1991 | Shimoyama et al. | 5,462,521 A | 10/1995 | Brucker et al. |
| 4,995,877 A | 2/1991 | Ams et al. | 5,472,441 A | 12/1995 | Edwards et al. |
| 5,015,227 A | 5/1991 | Broadwin et al. | 5,472,443 A | 12/1995 | Cordis et al. |
| 5,019,176 A | 5/1991 | Brandhorst, Jr. | 5,478,303 A | 12/1995 | Folry-Nolan et al. |
| 5,029,588 A | 7/1991 | Yock et al. | 5,480,399 A | 1/1996 | Hebborn |
| 5,087,257 A | 2/1992 | Farin | 5,483,952 A | 1/1996 | Aranyi |
| 5,103,804 A | 4/1992 | Abele et al. | 5,490,850 A | 2/1996 | Ellman et al. |
| 5,108,389 A | 4/1992 | Cosmescu | 5,496,312 A | 3/1996 | Klicek |
| 5,108,391 A | 4/1992 | Flachenecker | 5,496,313 A | 3/1996 | Gentelia |
| 5,122,137 A | 6/1992 | Lennox | 5,500,012 A | 3/1996 | Brucker et al. |
| 5,133,711 A | 7/1992 | Hagen | 5,500,616 A | 3/1996 | Ochi |
| 5,151,102 A | 9/1992 | Kamiyama et al. | 5,514,129 A | 5/1996 | Smith |
| 5,152,762 A | 10/1992 | McElhenney | 5,520,684 A | 5/1996 | Imran |
| 5,157,603 A | 10/1992 | Scheller et al. | 5,531,774 A | 7/1996 | Schulman et al. |
| 5,160,334 A | 11/1992 | Billings et al. | 5,534,018 A | 7/1996 | Wahlstrand et al. |
| 5,162,217 A | 11/1992 | Hartman | 5,536,267 A | 7/1996 | Edwards et al. |
| 5,167,658 A | 12/1992 | Ensslin | 5,540,681 A | 7/1996 | Strul et al. |
| 5,190,517 A | 3/1993 | Zieve et al. | 5,540,683 A | 7/1996 | Ichikawa |
| 5,196,008 A | 3/1993 | Kuenecke | 5,540,684 A | 7/1996 | Hassler, Jr. |
| 5,196,009 A | 3/1993 | Kirwan, Jr. | 5,540,724 A | 7/1996 | Cox |
| 5,201,900 A | 4/1993 | Nardella | 5,556,396 A | 9/1996 | Cohen et al. |
| 5,207,691 A | 5/1993 | Nardella | 5,558,671 A * | 9/1996 | Yates .......................... 606/38 |
| 5,230,623 A | 7/1993 | Guthrie et al. | 5,569,242 A | 10/1996 | Lax et al. |
| 5,233,515 A | 8/1993 | Cosman | 5,571,147 A | 11/1996 | Sluijter et al. |
| 5,249,121 A | 9/1993 | Baum et al. | 5,573,533 A | 11/1996 | Strul |
| RE34,432 E | 11/1993 | Bertrand | 5,584,830 A | 12/1996 | Ladd et al. |
| 5,267,994 A | 12/1993 | Gentelia et al. | 5,588,432 A | 12/1996 | Crowley |
| 5,267,997 A | 12/1993 | Farin | 5,594,636 A | 1/1997 | Schauder |
| 5,281,213 A | 1/1994 | Milder et al. | 5,596,466 A | 1/1997 | Ochi |
| 5,300,068 A | 4/1994 | Rosar et al. | 5,599,344 A | 2/1997 | Paterson |
| 5,300,070 A | 4/1994 | Gentelia | 5,599,345 A | 2/1997 | Edwards et al. |
| 5,318,563 A * | 6/1994 | Malis et al. .................. 606/38 | 5,605,150 A | 2/1997 | Radons et al. |
| 5,323,778 A | 6/1994 | Kandarpa et al. | 5,613,966 A | 3/1997 | Makower et al. |
| 5,324,283 A | 6/1994 | Heckele | 5,613,996 A | 3/1997 | Lindsay |
| 5,330,518 A | 7/1994 | Neilson et al. | 5,625,370 A | 4/1997 | D'Hont |
| 5,334,193 A | 8/1994 | Nardella | 5,626,575 A | 5/1997 | Crenner |
| 5,341,807 A | 8/1994 | Nardella | 5,628,745 A | 5/1997 | Bek |
| 5,342,356 A | 8/1994 | Ellman et al. | 5,643,330 A | 7/1997 | Holsheimer et al. |
| 5,342,357 A | 8/1994 | Nardella | 5,647,869 A | 7/1997 | Goble et al. |
| 5,342,409 A | 8/1994 | Mullett | 5,647,871 A | 7/1997 | Levine |
| 5,348,554 A | 9/1994 | Imran et al. | 5,651,780 A | 7/1997 | Jackson et al. |
| 5,370,645 A | 12/1994 | Klicek et al. | 5,658,322 A | 8/1997 | Fleming |
| 5,370,672 A | 12/1994 | Fowler et al. | 5,660,567 A | 8/1997 | Nierlich et al. |
| 5,370,675 A | 12/1994 | Edwards et al. | 5,688,267 A | 11/1997 | Panescu et al. |
| 5,372,596 A | 12/1994 | Klicek et al. | 5,690,692 A | 11/1997 | Fleming |
| 5,383,874 A | 1/1995 | Jackson | 5,693,042 A | 12/1997 | Bioarski et al. |
| 5,383,876 A | 1/1995 | Nardella | 5,694,304 A | 12/1997 | Telefus et al. |
| 5,383,917 A | 1/1995 | Desai et al. | 5,695,494 A | 12/1997 | Becker |
| 5,385,148 A | 1/1995 | Lesh et al. | 5,696,351 A | 12/1997 | Benn et al. |
| 5,396,062 A | 3/1995 | Eisentraut et al. | 5,702,386 A | 12/1997 | Stern et al. |
| 5,400,267 A | 3/1995 | Denen et al. | 5,702,429 A | 12/1997 | King |
| 5,403,311 A | 4/1995 | Abele et al. | 5,707,369 A | 1/1998 | Vaitekunas et al. |
| 5,403,312 A | 4/1995 | Yates et al. | 5,712,772 A | 1/1998 | Telefus et al. |
| 5,409,000 A | 4/1995 | Imran | 5,713,896 A | 2/1998 | Nardella |
| 5,409,006 A | 4/1995 | Buchholtz et al. | 5,720,744 A | 2/1998 | Eggleston et al. |
| 5,409,485 A | 4/1995 | Suda | 5,722,975 A | 3/1998 | Edwards et al. |
| 5,413,573 A | 5/1995 | Koivukangas | 5,733,281 A | 3/1998 | Nardella |
| 5,414,238 A | 5/1995 | Steigerwald et al. | 5,749,869 A | 5/1998 | Lindenmeier et al. |
| 5,417,719 A | 5/1995 | Hull et al. | 5,749,871 A | 5/1998 | Hood et al. |

| | | | | | | |
|---|---|---|---|---|---|---|
| 5,755,715 | A | 5/1998 | Stern | 6,273,886 B1 | 8/2001 | Edwards |
| 5,766,165 | A | 6/1998 | Gentelia et al. | 6,275,786 B1 | 8/2001 | Daners |
| 5,769,847 | A | 6/1998 | Panescu | 6,293,941 B1 | 9/2001 | Strul |
| 5,772,659 | A | 6/1998 | Becker et al. | 6,293,942 B1 | 9/2001 | Goble et al. |
| 5,792,138 | A | 8/1998 | Shipp | 6,306,131 B1 | 10/2001 | Hareyama et al. |
| 5,797,802 | A | 8/1998 | Nowak | 6,306,134 B1 | 10/2001 | Goble et al. |
| 5,797,902 | A | 8/1998 | Netherly | 6,309,386 B1 | 10/2001 | Bek |
| 5,814,092 | A | 9/1998 | King | 6,325,799 B1 | 12/2001 | Goble |
| 5,817,093 | A | 10/1998 | Williamson, IV et al. | 6,337,998 B1 | 1/2002 | Behl et al. |
| 5,820,568 | A | 10/1998 | Willis | 6,338,657 B1 | 1/2002 | Harper et al. |
| 5,827,271 | A | 10/1998 | Buysse et al. | 6,350,262 B1 | 2/2002 | Ashley |
| 5,830,212 | A | 11/1998 | Cartmell | 6,358,245 B1 | 3/2002 | Edwards |
| 5,836,943 | A * | 11/1998 | Miller, III .................... 606/34 | 6,364,877 B1 | 4/2002 | Goble et al. |
| 5,836,990 | A | 11/1998 | Li | 6,383,183 B1 | 5/2002 | Sekino et al. |
| 5,846,236 | A | 12/1998 | Lindenmeier et al. | 6,398,779 B1 | 6/2002 | Buysse et al. |
| 5,868,737 | A | 2/1999 | Taylor et al. | 6,398,781 B1 | 6/2002 | Goble et al. |
| 5,868,739 | A | 2/1999 | Lindenmeier et al. | 6,402,741 B1 | 6/2002 | Keppel et al. |
| 5,868,740 | A | 2/1999 | LeVeen et al. | 6,402,743 B1 | 6/2002 | Orszulak et al. |
| 5,871,481 | A | 2/1999 | Kannenberg et al. | 6,416,509 B1 | 7/2002 | Goble et al. |
| 5,897,552 | A | 4/1999 | Edwards et al. | 6,436,096 B1 | 8/2002 | Hareyama |
| 5,908,444 | A | 6/1999 | Azure | 6,451,015 B1 | 9/2002 | Rittman, III et al. |
| 5,913,882 | A | 6/1999 | King | 6,458,121 B1 | 10/2002 | Rosenstock |
| 5,921,982 | A | 7/1999 | Lesh et al. | 6,464,689 B1 | 10/2002 | Qin |
| 5,925,070 | A | 7/1999 | King et al. | 6,464,696 B1 | 10/2002 | Oyama |
| 5,931,836 | A | 8/1999 | Hatta et al. | 6,506,189 B1 | 1/2003 | Rittman, III et al. |
| 5,938,690 | A | 8/1999 | Law et al. | 6,508,815 B1 | 1/2003 | Strul |
| 5,948,007 | A | 9/1999 | Starkebaum et al. | 6,511,476 B2 | 1/2003 | Hareyama |
| 5,951,545 | A | 9/1999 | Schilling | 6,511,478 B1 | 1/2003 | Burnside et al. |
| 5,951,546 | A | 9/1999 | Lorentzen | 6,524,308 B1 | 2/2003 | Muller et al. |
| 5,954,686 | A | 9/1999 | Garito et al. | 6,547,786 B1 | 4/2003 | Goble |
| 5,954,717 | A | 9/1999 | Behl et al. | 6,558,376 B2 | 5/2003 | Bishop |
| 5,954,719 | A | 9/1999 | Chen et al. | 6,562,037 B2 | 5/2003 | Paton |
| 5,961,344 | A | 10/1999 | Rosales et al. | 6,565,559 B2 | 5/2003 | Eggleston |
| 5,971,980 | A | 10/1999 | Sherman | 6,573,248 B2 | 6/2003 | Ramasamy et al. |
| 5,976,128 | A | 11/1999 | Schilling et al. | 6,575,969 B1 | 6/2003 | Rittman, III et al. |
| 5,983,141 | A | 11/1999 | Sluijter et al. | 6,582,427 B1 | 6/2003 | Goble et al. |
| 6,010,499 | A | 1/2000 | Cobb | 6,620,157 B1 | 9/2003 | Dabney et al. |
| 6,014,581 | A | 1/2000 | Whayne et al. | 6,623,423 B2 | 9/2003 | Sakurai |
| 6,033,399 | A | 3/2000 | Gines | 6,635,057 B2 | 10/2003 | Harano |
| 6,044,283 | A | 3/2000 | Fein et al. | 6,648,883 B2 | 11/2003 | Francischelli |
| 6,053,910 | A | 4/2000 | Fleenor | 6,652,514 B2 | 11/2003 | Ellman |
| 6,053,912 | A | 4/2000 | Panescu et al. | 6,663,623 B1 | 12/2003 | Oyama et al. |
| 6,056,745 | A | 5/2000 | Panescu et al. | 6,663,624 B2 | 12/2003 | Edwards |
| 6,056,746 | A | 5/2000 | Goble et al. | 6,666,860 B1 | 12/2003 | Takahashi |
| 6,063,075 | A | 5/2000 | Mihori | 6,679,875 B2 | 1/2004 | Honda |
| 6,063,078 | A | 5/2000 | Wittkampf | 6,682,527 B2 | 1/2004 | Strul |
| 6,068,627 | A | 5/2000 | Orszulak et al. | 6,685,700 B2 | 2/2004 | Behl |
| 6,074,386 | A | 6/2000 | Goble et al. | 6,685,701 B2 | 2/2004 | Orszulak et al. |
| 6,080,149 | A | 6/2000 | Huang et al. | 6,692,489 B1 | 2/2004 | Heim |
| 6,093,186 | A | 7/2000 | Goble | 6,712,813 B2 | 3/2004 | Ellman |
| RE36,871 | E | 9/2000 | Epstein | 6,730,080 B2 | 5/2004 | Harano |
| 6,113,591 | A | 9/2000 | Whayne et al. | 6,733,495 B1 | 5/2004 | Bek |
| 6,113,596 | A | 9/2000 | Hooven | 6,733,498 B2 | 5/2004 | Paton |
| 6,123,702 | A | 9/2000 | Swanson et al. | 6,740,079 B1 | 5/2004 | Eggers |
| 6,132,429 | A | 10/2000 | Baker | 6,740,085 B2 | 5/2004 | Hareyama |
| 6,142,992 | A | 11/2000 | Cheng et al. | 6,783,523 B2 | 8/2004 | Qin |
| 6,162,217 | A | 12/2000 | Kannenberg et al. | 6,790,206 B2 | 9/2004 | Panescu |
| 6,171,304 | B1 | 1/2001 | Netherly et al. | 6,796,981 B2 | 9/2004 | Wham |
| 6,203,541 | B1 | 3/2001 | Keppel | 6,824,539 B2 | 11/2004 | Novak |
| 6,210,403 | B1 | 4/2001 | Klicek | 6,830,569 B2 | 12/2004 | Thompson |
| 6,228,080 | B1 | 5/2001 | Gines | 6,843,789 B2 | 1/2005 | Goble |
| 6,228,081 | B1 | 5/2001 | Goble | 6,849,073 B2 | 2/2005 | Hoey |
| 6,231,569 | B1 | 5/2001 | Bek | 6,855,141 B2 | 2/2005 | Lovewell |
| 6,235,020 | B1 | 5/2001 | Cheng et al. | 6,855,142 B2 | 2/2005 | Harano |
| 6,238,387 | B1 | 5/2001 | Miller, III | 6,860,881 B2 | 3/2005 | Sturm |
| 6,238,388 | B1 | 5/2001 | Ellman | 6,864,686 B2 | 3/2005 | Novak |
| 6,241,725 | B1 | 6/2001 | Cosman | 6,875,210 B2 | 4/2005 | Refior |
| 6,245,065 | B1 | 6/2001 | Panescu | 6,893,435 B2 | 5/2005 | Goble |
| 6,246,912 | B1 | 6/2001 | Sluijter et al. | 7,044,948 B2 | 5/2006 | Keppel |
| 6,251,106 | B1 | 6/2001 | Becker et al. | 7,060,063 B2 | 6/2006 | Marion et al. |
| 6,258,085 | B1 | 7/2001 | Eggleston | 7,063,692 B2 | 6/2006 | Sakurai et al. |
| 6,261,285 | B1 | 7/2001 | Novak | 7,066,933 B2 | 6/2006 | Hagg |
| 6,261,286 | B1 | 7/2001 | Goble et al. | 7,131,860 B2 | 11/2006 | Sartor et al. |

| | | | | | | |
|---|---|---|---|---|---|---|
| 7,137,980 | B2 | 11/2006 | Buysse et al. | DE | 2823291 | 11/1979 |
| 2001/0014804 | A1 | 8/2001 | Goble et al. | DE | 2946728 | 5/1981 |
| 2001/0031962 | A1 | 10/2001 | Eggleston | DE | 3143421 | 5/1982 |
| 2002/0035353 | A1 | 3/2002 | Edwards et al. | DE | 3045996 | 7/1982 |
| 2002/0035364 | A1 | 3/2002 | Schoenman et al. | DE | 3120102 | 12/1982 |
| 2002/0068932 | A1 | 6/2002 | Edwards | DE | 3510586 | 10/1986 |
| 2002/0107517 | A1 | 8/2002 | Witt et al. | DE | 3604823 | 8/1987 |
| 2002/0111624 | A1 | 8/2002 | Witt et al. | DE | 390937 | 4/1989 |
| 2002/0193787 | A1 | 12/2002 | Qin | DE | 3904558 | 8/1990 |
| 2003/0004510 | A1 | 1/2003 | Wham et al. | DE | 3942998 | 7/1991 |
| 2003/0060818 | A1 | 3/2003 | Kannenberg | DE | 4339049 A1 | 5/1995 |
| 2003/0078572 | A1 | 4/2003 | Pearson et al. | DE | 19717411 | 11/1998 |
| 2003/0139741 | A1 | 7/2003 | Goble et al. | DE | 19717411 A1 | 11/1998 |
| 2003/0153908 | A1 | 8/2003 | Goble | DE | 19848540 A1 | 5/2000 |
| 2003/0163123 | A1 | 8/2003 | Goble | EP | 246350 | 11/1987 |
| 2003/0163124 | A1 | 8/2003 | Goble | EP | 310431 | 4/1989 |
| 2003/0171745 | A1 | 9/2003 | Francischelli | EP | 325456 | 7/1989 |
| 2003/0199863 | A1 | 10/2003 | Swanson | EP | 336742 | 10/1989 |
| 2003/0225401 | A1 | 12/2003 | Eggers et al. | EP | 390937 | 10/1990 |
| 2004/0002745 | A1 | 1/2004 | Flemming | EP | 556705 | 8/1993 |
| 2004/0015216 | A1 | 1/2004 | DeSisto | EP | 0569130 A1 | 11/1993 |
| 2004/0019347 | A1 | 1/2004 | Sakurai | EP | 608609 | 8/1994 |
| 2004/0024395 | A1 | 2/2004 | Ellman | EP | 836868 | 4/1998 |
| 2004/0030328 | A1 | 2/2004 | Eggers | EP | 878169 | 11/1998 |
| 2004/0030330 | A1 | 2/2004 | Brassell et al. | EP | 1293171 | 3/2003 |
| 2004/0044339 | A1 | 3/2004 | Beller | EP | 0880220 B1 | 6/2006 |
| 2004/0049179 | A1 | 3/2004 | Francischelli | FR | 1275415 | 10/1961 |
| 2004/0054365 | A1 | 3/2004 | Goble | FR | 1347865 | 11/1963 |
| 2004/0068304 | A1 | 4/2004 | Paton | FR | 2313708 | 12/1976 |
| 2004/0082946 | A1 | 4/2004 | Malis | FR | 2502935 | 10/1982 |
| 2004/0095100 | A1 | 5/2004 | Thompson | FR | 2517953 | 6/1983 |
| 2004/0097912 | A1 | 5/2004 | Gonnering | FR | 2573301 | 5/1986 |
| 2004/0097914 | A1 | 5/2004 | Pantera | GB | 607850 | 9/1948 |
| 2004/0097915 | A1 | 5/2004 | Refior | GB | 855459 | 11/1960 |
| 2004/0116919 | A1 | 6/2004 | Heim | GB | 902775 | 8/1962 |
| 2004/0133189 | A1 | 7/2004 | Sakurai | GB | 2164473 | 3/1986 |
| 2004/0138653 | A1 | 7/2004 | Dabney | GB | 2214430 | 9/1989 |
| 2004/0138654 | A1 | 7/2004 | Goble | GB | 2358934 A | 8/2001 |
| 2004/0172016 | A1 | 9/2004 | Bek | SU | 166452 | 1/1965 |
| 2004/0230189 | A1 | 11/2004 | Keppel | SU | 727201 | 4/1980 |
| 2004/0243120 | A1 | 12/2004 | Orszulak et al. | WO | WO92/06642 | 4/1992 |
| 2004/0260279 | A1 | 12/2004 | Goble | WO | WO93/24066 | 12/1993 |
| 2005/0004564 | A1 | 1/2005 | Wham | WO | WO94/24949 | 11/1994 |
| 2005/0004569 | A1 | 1/2005 | Witt et al. | WO | WO94/28809 | 12/1994 |
| 2005/0021022 | A1 | 1/2005 | Sturm et al. | WO | WO95/09577 | 4/1995 |
| 2005/0101951 | A1 | 5/2005 | Wham | WO | WO95/19148 | 7/1995 |
| 2005/0113818 | A1 | 5/2005 | Sartor | WO | WO96/02180 | 2/1996 |
| 2005/0113819 | A1 | 5/2005 | Wham | WO | WO96/04860 | 2/1996 |
| 2005/0149151 | A1 | 7/2005 | Orszulak | WO | WO96/08794 | 3/1996 |
| 2005/0182398 | A1 | 8/2005 | Paterson | WO | WO96/18349 | 6/1996 |
| 2005/0197659 | A1 | 9/2005 | Bahney | WO | WO96/29946 | 10/1996 |
| 2005/0203504 | A1 | 9/2005 | Wham et al. | WO | WO96/39914 | 12/1996 |
| 2006/0025760 | A1 | 2/2006 | Podhajsky | WO | WO97/06739 | 2/1997 |
| 2006/0079871 | A1 | 4/2006 | Plaven et al. | WO | WO97/06740 | 2/1997 |
| 2006/0161148 | A1 | 7/2006 | Behnke | WO | WO97/06855 | 2/1997 |
| 2006/0178664 | A1 | 8/2006 | Keppel | WO | WO97/17029 | 5/1997 |
| 2006/0224152 | A1 | 10/2006 | Behnke et al. | WO | WO02/11634 | 2/2002 |
| 2006/0281360 | A1 | 12/2006 | Sartor et al. | WO | WO02/45589 | 6/2002 |
| | | | | WO | WO02/47565 | 6/2002 |
| | | FOREIGN PATENT DOCUMENTS | | WO | WO02/088128 | 7/2002 |
| | | | | WO | WO2005048809 A1 | 6/2005 |
| DE | 1099658 | 2/1961 | | | | |
| DE | 1139927 | 11/1962 | | | | |
| DE | 1149832 | 6/1963 | | | | |
| DE | 1439302 | 1/1969 | | | | |
| DE | 2439587 | 2/1975 | | | | |
| DE | 2455174 | 5/1975 | | | | |
| DE | 2407559 | 8/1975 | | | | |
| DE | 2602517 | 7/1976 | | | | |
| DE | 2504280 | 8/1976 | | | | |
| DE | 2540968 | 3/1977 | | | | |
| DE | 2820908 | 11/1978 | | | | |
| DE | 2803275 | 8/1979 | | | | |

OTHER PUBLICATIONS

Bergdahl and Vallfors "Studies on Coagulation and the Development of an Automatic Computerized Bipolar Coagulator" Journal of Neurosurgery, 75:1, 148 151, Jul. 1991.

Chicharo et al. "A Sliding Goertzel Algorith" Aug. 1996, pp. 283-297 Signal Processing, Elsevier Science Publishers B.V. Amsterdam, NL. vol. 52 No. 3.

Ogden "Goertzel Alternative to the Fourier Transform" Jun. 1993 pp. 485-487 Electronics World; Reed Business Publishing, Sutton, Surrey, GB vol. 99, No. 1687.

International Search Report—PCT/US03/37110.
International Search Report—PCT/US03/37310.
International Search Report—EP4009964.
International Search Report—EP98300964.8.
International Search Report—EP04015981.6.
Chicharo et al. "A Sliding Goertzel Algorith" Aug. 1996, pp. 283-297 Signal Processing, Elsevier Science Publishers B.V. Amsterdam, NL vol. 52 No. 3.
Ogden Goertzel Alternative to the Fourier Transform: Jun. 1993 pp. 485-487 Electronics World; Reed Business Publishing, Sutton, Surrey, BG vol. 99, No. 9. 1687.
Medtrex Brochure "The O.R. Pro 300" 1 p. Sep. 1998.
Valleylab Brochure "Valleylab Electroshield Monitoring System" 2 pp. Nov. 1995.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences-Yingyong Kexue Xuebao, Shanghai CN, vol. 23 No. 2; (Mar. 2005); 160-164.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium interstitial Implants" Medical Physics, 9 (3), May/Jun. 1982.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15:(1984) pp. 945-950.

Geddes et al., "The Measurement of Physiologic Events by Electrical Impedance" Am. J. MI, Jan. Mar. 1964, pp. 16-27.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Sugita et al., "Bipolar Coagulator with Automatic Thermocontrol" J. Neurosurg., vol. 41, Dec. 1944, pp. 777-779.

Wald et al., "Accidental Burns", JAMA, Aug. 16, 1971, vol. 217, No. 7, pp. 916-921.

* cited by examiner

VESSEL SEALING SYSTEM

CROSS REFERENCE TO RELATED APPLICATIONS

The present application is a continuation-in-part application of U.S. patent application Ser. No. 10/073,761 filed Feb. 11, 2002 entitled "Vessel Sealing System", by Robert Wham et al., which is now U.S. Pat. No. 6,796,981, which claims priority from U.S. patent application Ser. No. 09/408,944 also entitled "Vessel Sealing System," by Robert Wham et al., which is now U.S. Pat. No. 6,398,779, and which claims priority to U.S. Provisional Patent Application Ser. No. 60/105,417 filed on Oct. 23, 1998. The disclosure of each Patent Application is incorporated by reference herein in its entirety.

FIELD

This invention relates generally to medical instruments and, in particular, to generators that provide radio frequency (RF) energy useful in sealing tissue and vessels during electrosurgical and other procedures.

BACKGROUND

Electrosurgical generators are employed by surgeons to cut and coagulate the tissue of a patient. High frequency electrical power, which may be also referred to as radio frequency (RF) power or energy, is produced by the electrosurgical generator and applied to the tissue by an electrosurgical tool. Both monopolar and bipolar configurations are commonly used during electrosurgical procedures.

Electrosurgical techniques can be used to seal small diameter blood vessels and vascular bundles. Another application of electrosurgical techniques is in tissue fusion wherein two layers of tissue are grasped and clamped together by a suitable electrosurgical tool while the electrosurgical RF energy is applied. The two layers of tissue are then fused together.

At this point it is significant to note that the process of coagulating small vessels is fundamentally different than vessel sealing or tissue fusion. For the purposes herein the term coagulation can be defined as a process of desiccating tissue wherein the tissue calls are ruptured and dried. Vessel sealing or tissue fusion can both be defined as desiccating tissue by the process of liquefying the collagen in the tissue so that it crosslinks and reforms into a fused mass. Thus, the coagulation of small vessels if generally sufficient to close them, however, larger vessels normally need to be sealed to assure permanent closure.

However, and as employed herein, the term "electrosurgical desiccation" is intended to encompass any tissue desiccation procedure, including electrosurgical coagulation, desiccation, vessel sealing, and tissue fusion.

One of the problems that can arise from electrosurgical desiccation is undesirable tissue damage due to thermal effects, wherein otherwise healthy tissue surrounding the tissue to which the electrosurgical energy is being applied is thermally damaged by an effect known in the art as "thermal spread". During the occurrence of thermal spread excess heat from the operative site can be directly conducted to the adjacent tissue, and/or the release of steam from the tissue being treated at the operative site can result in damage to the surrounding tissue.

It can be appreciated that it would be desirable to provide an electrosurgical generator that limited the possibility of the occurrence of thermal spread.

Another problem that can arise with conventional electrosurgical techniques is a buildup of eschar on the electrosurgical tool or instrument. Eschar is a deposit that forms on working surface(s) of the tool, and results from tissue that is electrosurgically desiccated and then charred. One result of the buildup of eschar is a reduction in the effectiveness of the surgical tool. The buildup of eschar on the electrosurgical tool can be reduced if less heat is developed at the operative site.

It has been well established that a measurement of the electrical impedance of tissue provides an indication of the state of desiccation of the tissue, and this observation has been utilized in some electrosurgical generators to automatically terminate the generation of electrosurgical power based on a measurement of tissue impedance.

At least two techniques for determining an optimal amount of desiccation are known by those skilled in this art. One technique sets a threshold impedance, and terminates electrosurgical power when the measured tissue impedance crosses the threshold. A second technique terminates the generation of electrosurgical power based on dynamic variations in the tissue impedance.

A discussion of the dynamic variations of tissue impedance can be found in a publication entitled "Automatically Controlled Bipolar Electrocoagulation", *Neurosurgical Review*, 7:2-3, pp. 187-190, 1984, by Vallfors and Bergdahl. FIG. 2 of this publication depicts the impedance as a function of time during the heating of a tissue, and the authors reported that the impedance value of tissue was observed to be near to a minimum value at the moment of coagulation. Based on this observation, the authors suggest a micro-computer technique for monitoring the minimum impedance and subsequently terminating the output power to avoid charring the tissue.

Another publication by the same authors, "Studies on Coagulation and the Development of an Automatic Computerized Bipolar Coagulator", *Journal of Neurosurgery*, 75:1, pp. 148-151, July 1991, discusses the impedance behavior of tissue and its application to electrosurgical vessel sealing, and reports that the impedance has a minimum value at the moment of coagulation.

The following U.S. Patents are also of interest in this area. U.S. Pat. No. 5,540,684, Hassler, Jr. addresses the problem associated with turning off the RF energy output automatically after the tissue impedance has fallen from a predetermined maximum, subsequently risen from a predetermined minimum and then reached a particular threshold. A storage device records maximum and minimum impedance values, and a circuit determines the threshold. U.S. Pat. No. 5,472,443, Cordis et al., discusses a variation of tissue impedance with temperature, wherein the impedance is shown to fall, and then to rise, as the temperature is increased. FIG. 2 of this patent shows a relatively lower temperature Region A where salts contained in body fluids are believed to dissociate, thereby decreasing the electrical impedance. A relatively next higher temperature Region B is where the water in the tissue boils away, causing the impedance to rise. The next relatively higher temperature Region C is where the tissue becomes charred, which results in a slight lowering of the electrical impedance. U.S. Pat. No. 4,191,188, Belt et al., discloses the use of two timers whose duty cycles are simultaneously and proportionately adjusted so that high frequency signal bursts are constantly centered about the peak power point, regardless of duty cycle variations.

Also of interest is U.S. Pat. No. 5,827,271, Buysse et al., "Energy Delivery System for Vessel Sealing", which employs a surgical tool capable of grasping a tissue and applying an appropriate amount of closure force to the tissue, and for then conducting electrosurgical energy to the tissue concurrently with the application of the closure force. FIG. 2 of this patent, shown herein as FIG. 1 for depicting the prior art, illustrates a set of power curves which represent the electrosurgical power delivered to the tissue as a function of the tissue impedance. At low impedances, the electrosurgical power is increased by rapidly increasing the output current. The increase in electrosurgical power is terminated when a first impedance breakpoint, labeled as 1, is reached (e.g. <20 ohms). Next, the electrosurgical power is hold approximately constant until proteins in the vessels and other tissues have melted. The impedance at which this segment ends varies in accordance with the magnitude of the RMS power. For example, where the maximum RMS power is approximately 125 Watts, the segment (B) ends at about 128 ohms. When a lower power is used (e.g., 75 Watts), the segment (C) may end at an impedance value of 256 ohms. Next, the output power is lowered to less than one half the maximum value, and the lower power delivery is terminated when a second impedance breakpoint is reached ($2.048 \times 10^3$ ohms). Alternatives to using the impedance for determining the second breakpoint are the use of I-V phase angle, or the magnitude of the output current.

Based on the foregoing it should be evident that electrosurgery requires the controlled application of RF energy to an operative tissue site. To achieve successful clinical results during surgery, the electrosurgical generator should produce a controlled output RF signal having an amplitude and wave shape that is applied to the tissue within predetermined operating levels. However, problems can arise during electrosurgery when rapid desiccation of tissue occurs resulting in excess RF levels being applied to the tissue. These excess levels produce less than desirable tissue effects, which can increase thermal spread, or can cause tissue charring and may shred and disintegrate tissue. It would be desirable to provide a system with more controlled output to improve vessel sealing and reduce damage to surrounding tissue. The factors that affect vessel sealing include the surgical instrument utilized, as well as the generator for applying RF energy to the instrument jaws. It has been recognized that the gap between the instrument jaws and the pressure of the jaws against the tissue affect tissue sealing because of their impact on current flow. For example, insufficient pressure or an excessive gap will not supply sufficient energy to the tissue and could result in an inadequate seal.

However, it has also been recognized that the application of RF energy also affects the seal. For example, pulsing of RF energy will improve the seal. This is because the tissue loses moisture as it desiccates and by stopping or significantly lowering the output the generator between pulses, this allows some moisture to return to the tissue for the application of next RF pulse. It has also been recognized by the inventors that varying each pulse dependent on certain parameters is also advantageous in providing an improved seal. Thus, it would be advantageous to provide a vessel sealing system which better controls RF energy and which can be varied at the outset of the procedure to accommodate different tissue structures, and which can further be varied during the procedure itself to accommodate changes in the tissue as it desiccates.

An accommodation for overvoltage clamping is also desirable. In this regard, conventional overvoltage techniques use a means of clamping or clipping the excess overvoltage using avalanche devices such as diodes, zener diodes and transorbs so as to limit the operating levels. In these techniques the excess energy, as well as the forward conduction energy, is absorbed by the protection device and inefficiently dissipated in the form of heat. More advanced prior art techniques actively clamp only the excess energy using a predetermined comparator reference value, but still absorb and dissipate the excess energy in the form of heat.

U.S. Pat. No. 5,594,636 discloses a system for AC to AC power conversion using switched commutation. This system addresses overvoltage conditions which occur during switched commutation by incorporating an active output voltage sensing and clamping using an active clamp voltage regulator which energizes to limit the output. The active clamp switches in a resistive load to dissipate the excess energy caused by the overvoltage condition.

Other patents in this area include U.S. Pat. No. 5,500,616, which discloses an overvoltage clamp circuit, and U.S. Pat. No. 5,596,466, which discloses an isolated half-bridge power module. Both of these patents identify output overvoltage limiting for all power devices, and overvoltage limit protection is provided for power devices by using proportionately scaled zeners to monitor and track the output off voltage of each device to prevent power device failure. The zener device is circuit configured such that it provides feedback to the gate of the power device, When zener avalanche occurs the power device partially turns on, absorbing the excess overvoltage energy in conjunction with the connective load.

Reference can also be had to U.S. Pat. No. 4,646,222 for disclosing an inverter incorporating overvoltage clamping. Overvoltage clamping is provided by using diode clamping devices referenced to DC power sources. The DC power sources provide a predetermined reference voltage to clamp the overvoltage condition, absorbing the excess energy through clamp diodes which dissipate the excess voltage in the form of heat.

It would be advantageous as to provide an electrosurgical generator having improved overvoltage limit and transient energy suppression.

SUMMARY

The foregoing and other problems are overcome by methods and apparatus in accordance with embodiments disclosed herein.

An electrosurgical generator includes a controlling data processor that executes software algorithms providing a number of new and useful features. These features preferably include the generation of an initial pulse, that is a low power pulse of RF energy that is used to sense at least one electrical characteristic of the tissue prior to starting an electrosurgical desiccation cycle, such as a tissue sealing cycle. The sensed electrical characteristic is then used as an input into the determination of initial sealing param ters, thereby making the sealing procedure adaptive to the characteristics of the tissue to be sealed. Another feature preferably provided measures the time required for the tissue to begin desiccating, preferably by observing an electrical transient at the beginning of an RF energy pulse, to determine and/or modify further seal parameters. Another preferable feature performs a tissue temperature control function by adjusting the duty cycle of the RF energy pulses applied to the tissue, thereby avoiding the problems that can result from excessive tissue heating. A further preferable feature controllably decreases the RF pulse voltage with each pulse of RF energy so that as the tissue desiccates and shrinks (thereby reducing the spacing between the surgical tool electrodes), arcing between the electrodes is avoided, as is the tissue destruction that may result from uncontrolled arcing. Preferably a Seal Intensity operator control is provided that enables the operator to control the sealing of tissue by varying parameters other than simply the RF power.

The system disclosed herein preferably further provides a unique method for overvoltage limiting and transient energy suppression. An electrosurgical system uses dynamic, real-time automatic detuning of the RF energy delivered to the tissue of interest. More specifically, this technique automatically limits excess output RF voltages by dynamically changing the tuning in a resonant source of RF electrosurgical energy, and by altering the shape of the RF source signal used to develop the output RF signal. The inventive technique limits the excess output transient RF energy by a resonant detuning of the generator. This occurs in a manner which does not clip or significantly distort the generated RF output signal used in a clinical environment for electrosurgical applications.

A method for electrosurgically sealing a tissue, in accordance with this disclosure, preferably includes the steps of (A) applying an initial pulse of RF energy to the tissue, the pulse having characteristics selected so as not to appreciably heat the tissue; (B) measuring a value of at least one electrical characteristic of the tissue in response to the applied first pulse; (C) in accordance with the measured at least one electrical characteristic, determining an initial set of pulse parameters for use during the next RF energy pulse that is applied to the tissue; and (D) varying the pulse parameters of subsequent RF energy pulses individually in accordance with at least one characteristic of an electrical transient that occurs during each individual subsequent RF energy pulse. The method terminates the generation of subsequent RF energy pulses based upon a reduction in the output voltage or upon a determination that the electrical transient is absent.

The at least one characteristic that controls the variation of the pulse parameters is preferably a width of the electrical transient that occurs at the beginning of each subsequent RF energy pulse. The initial set of pulse parameters include a magnitude of a starting current and voltage, and the pulse parameters that are varied include a pulse duty cycle and a pulse amplitude. Preferably, the subsequent RF energy pulses are each reduced or modified in amplitude by a controlled amount from a previous RF energy pulse, thereby compensating for a decrease in the spacing between the surgical tool electrodes due to desiccation of the tissue between the electrodes.

The step of determining an initial set of pulse parameters preferably includes a step of using the measured value of at least one electrical characteristic of the tissue to readout the initial set of pulse parameters from an entry in a lookup table.

The step of determining an initial set of pulse parameters may also preferably include a step of reading out the initial set of pulse parameters from an entry in one of a plurality of lookup tables, where the lookup table is selected either manually or automatically, based on the electrosurgical instrument or tool that is being used.

The method also preferably includes a step of modifying predetermined ones of the pulse parameters in accordance with a control input from an operator. The predetermined ones of the pulse parameters that are modified include a pulse power, a pulse starting current and voltage level, a pulse voltage decay scale factor, and a pulse dwell time.

Preferably a circuit is coupled to the output of the electrosurgical generator for protecting the output against an overvoltage-condition, and includes a suppressor that detunes a tuned resonant circuit at the output for reducing a magnitude of a voltage appearing at the output. In accordance with this aspect of the disclosure, the circuit has a capacitance network in parallel with an inductance that forms a portion of the output stage of the generator. A voltage actuated switch, such as a transorb, couples an additional capacitance across the network upon an occurrence of an overvoltage condition, thereby detuning the resonant network and reducing the magnitude of the voltage output.

BRIEF DESCRIPTION OF THE DRAWINGS

The above set forth and other features of the invention are made more apparent in the ensuing Detailed Description when read in conjunction with the attached Drawings, wherein:

FIG. 9A illustrates a Seal Intensity control that forms a part of this disclosure, while FIGS. 9B and 9C show a preferred variation in certain parameters from the seal parameter LUT based on different Seal Intensity settings;

DETAILED DESCRIPTION OF THE PREFERRED EMBODIMENT

Figure 1A:
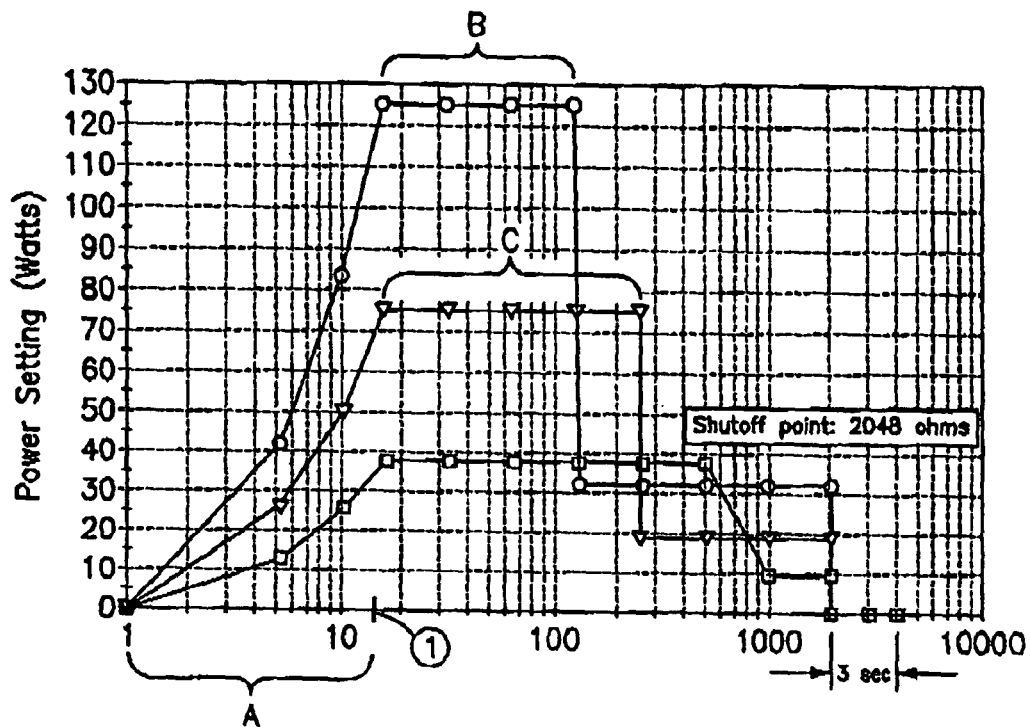
FIG. 1A is a graph that plots output power versus tissue impedance (Z) in ohms, in accordance with the operation of a prior art electrosurgical generator.
Figure 2:
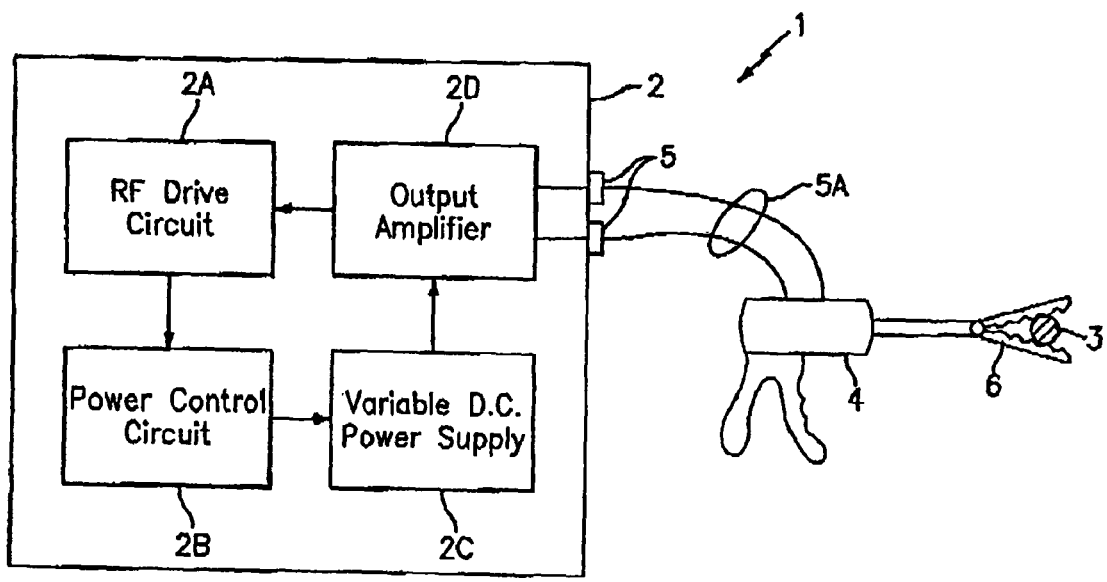
FIG. 2 is a simplified block diagram of an electrosurgical system that can be used to practice the teachings of this disclosure.

An electrosurgical system 1, which can be used to practice this invention, is shown in FIG. 2. The system I can be used for sealing vessels 3 and other tissues of a patient, including ducts, veins, arteries and vascular tissue. The system 1 includes an electro-surgical generator 2 and a surgical tool, also referred to herein as a surgical instrument 4. The surgical instrument 4 is illustrated by way of example, and as will become apparent from the discussion below, other instruments can be utilized. The electrosurgical generator 2, which is of most interest to the teachings herein, includes several interconnected sub-units, including an RF drive circuit 2A, a power control circuit 2B, a variable D.C. power supply 2C and an output amplifier 2D. The surgical instrument 4 is electrically connected to the electrosurgical generator 2 using a plug 5 for receiving controlled electrosurgical power therefrom. The surgical instrument 4 has some type of end effector member 6, such as a forceps or hemostat, capable of grasping and holding the vessels and tissues of the patient. The member 6, also referred to simply as end effector 6, is assumed, in this embodiment, to be capable of applying and maintaining a relatively constant level of pressure on the vessel 3.

The member 6 is provided in the form of bipolar electrosurgical forceps using two generally opposing electrodes disposed on inner opposing surfaces of the member 6, and which are both electrically coupled to the output of the electrosurgical generator 2. During use, different electric potentials are applied to each electrode. In that tissue is an electrical conductor, when the forceps are utilized to clamp or grasp the vessel 3 therebetween, the electrical energy output from the electrosurgical generator 2 is transferred through the intervening tissue. Both open surgical procedures and endoscopic surgical procedures can be performed with suitably adapted surgical instruments 4. It should also be noted that the member 6 could be monopolar forceps that utilize one active electrode, with the other (return) electrode or pad being attached externally to the patient, or a combination of bipolar and monopolar forceps.

Figure 3:
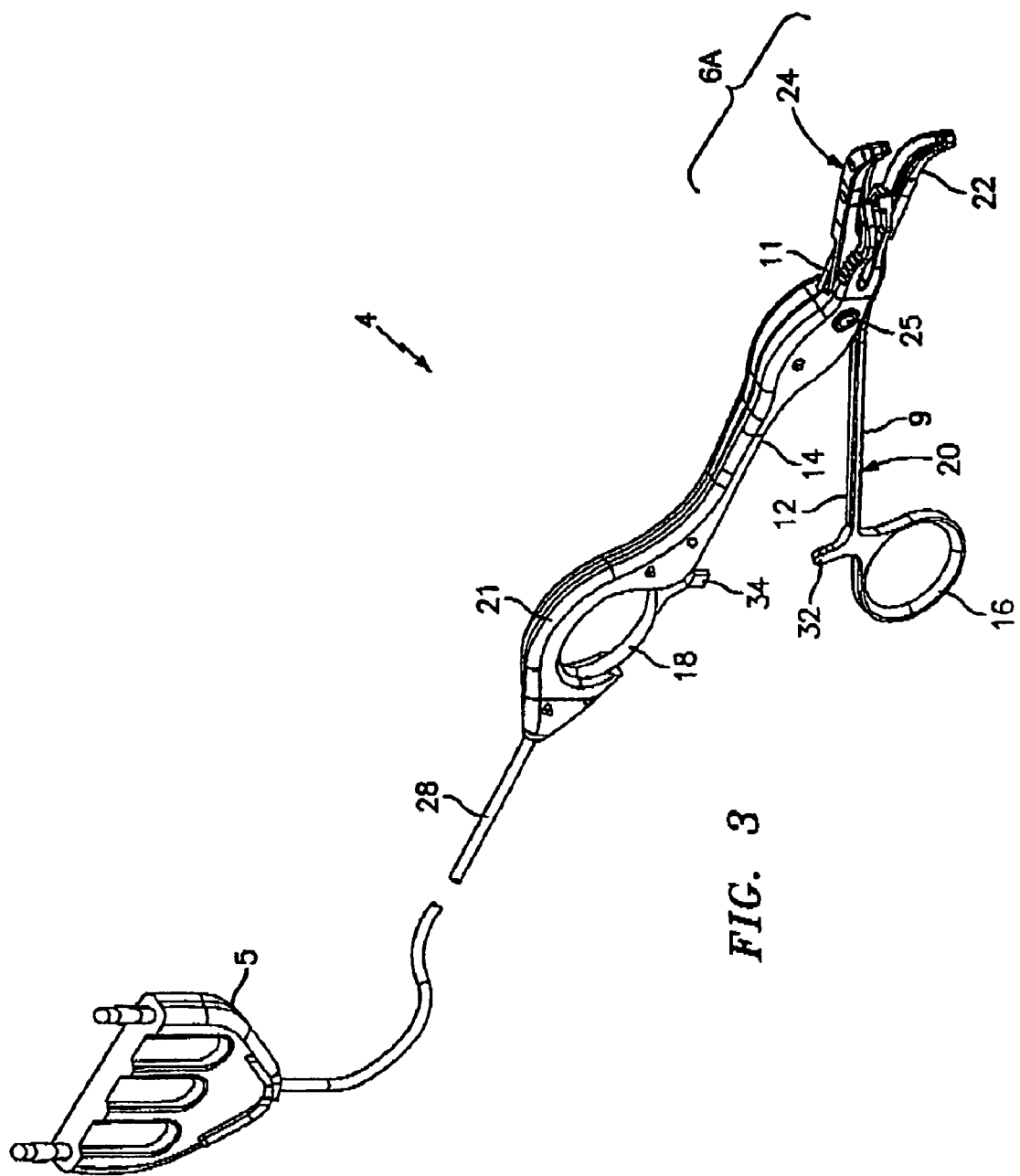
FIG. 3 is a perspective view of one embodiment of a surgical instrument having bipolar forceps that are suitable for practicing this disclosure.
Figure 4:
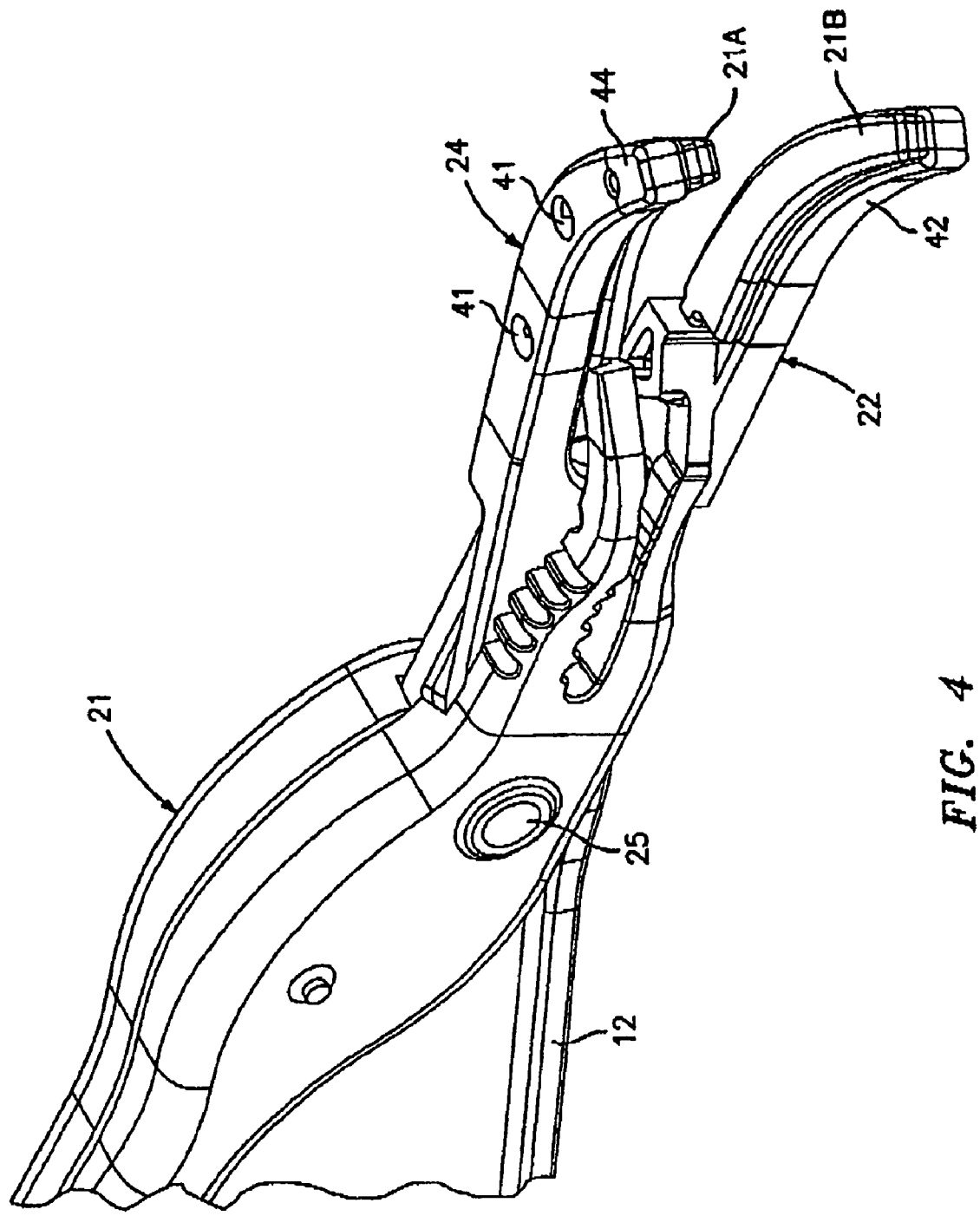
FIG. 4 is an enlarged, perspective view of a distal end of the bipolar forceps shown in FIG. 3.

By way of further explanation, FIG. 3 is a perspective view of one embodiment of the surgical instrument 4 having a bipolar end effector implemented as forceps 6A while FIG. 4 is an enlarged, perspective view of a distal end of the bipolar forceps 6A shown in FIG. 3.

Referring now to FIGS. 3 and 4, a bipolar surgical instrument 4 for use with open surgical procedures includes a mechanical forceps 20 and an electrode assembly 21. In the drawings and in the description which follows, the term "proximal", as is traditional, refers to the end of the instrument 4 which is closer to the user, while the term "distal" refers to the end which is further from the user.

Mechanical forceps 20 includes first and second members 9 and 11 which each have an elongated shaft 12 and 14, respectively. Shafts 12 and 14 each include a proximal end and a distal end. Each proximal end of each shaft portion 12, 14 includes a handle member 16 and 18 attached thereto to allow a user to effect movement of the two shaft portions 12 and 14 relative to one another. Extending from the distal end of each shaft portion 12 and 14 are end effectors 22 and 24, respectively. The end effectors 22 and 24 are movable relative to one another in response to movement of handle members 16 and 18. These end effectors members 6A can be referred to collectively as bipolar forceps.

Preferably, shaft portions 12 and 14 are affixed to one another at a point proximate the end effectors 22 and 24 about a pivot 25. As such, movement of the handles 16 and 18 imparts movement of the end effectors 22 and 24 from an open position, wherein the end effectors 22 and 24 are disposed in spaced relation relative to one another, to a clamping or closed position, wherein the end effectors 22 and 24 cooperate to grasp the tubular vessel 3 therebetween. Either one or both of the end effectors 22, 24 can be movable.

As is best seen in FIG. 4, end effector 24 includ s an upper or first jaw member 44 which has an inner facing surface and a plurality of mechanical interfaces disposed thereon which are dimensioned to releasable engage a portion of an electrode assembly 21, which may be disposable. Preferably, the mechanical interfaces include sockets 41 which are disposed at least partially through the inner facing surface of jaw member 44 and which are dimensioned to receive a complimentary detent attached to an upper electrode 21A of the disposable electrode assembly 21. The upper electrode 21A is disposed across from a corresponding lower electrode 21B. The end effector 22 includes a second or lower jaw member 42 which has an inner facing surface which opposes the inner facing surface of the first jaw member 44.

Preferably, shaft members 12 and 14 of the mechanical forceps 20 are designed to transmit a particular desired force to the opposing inner facing surfaces of the jaw members 22 and 24 when clamped. In particular, since the shaft members 12 and 14 effectively act together in a spring-like manner (i.e., bending that behaves like a spring), the length, width, height and deflection of the shaft members 12 and 14 directly impacts the overall transmitted force imposed on opposing jaw members 42 and 44. Preferably, jaw members 22 and 24 are more rigid than the shaft members 12 and 14 and the strain energy stored in the shaft members 12 and 14 provides a constant closure force between the jaw members 42 and 44.

Each shaft member 12 and 14 also includes a ratchet portion 32 and 34. Preferably, each ratchet, e.g., 32, extends from the proximal end of its respective shaft member 12 towards the other ratchet 34 in a g nerally vertically aligned manner such that the inner facing surfaces of each ratchet 32 and 34 abut one another when the end effectors 22 and 24 are moved from the open position to the closed position. Each ratchet 32 and 34 includes a plurality of flanges which project from the inner facing surface of each ratchet 32 and 34 such that the ratchets 32 and 34 can interlock in at least one position. In the embodiment shown in FIG. 3, the ratchets 32 and 34 interlock at several different positions. Preferably, each ratchet position holds a specific, i.e., constant, strain energy in the shaft members 12 and 14 which, in turn, transmits a specific force to the end effectors 22 and 24 and, thus, to the electrodes 21A and 21B. Also, preferably a stop is provided on one or both of the end effectors 22, 24 to maintain a preferred gap between the jaws.

In some cases it may be preferable to include other mechanisms to control and/or limit the movement of the jaw members 42 and 44 relative to one another. For example, a ratchet and pawl system could be utilized to segment the movement of the two handles into discrete units which, in turn, impart discrete movement to the jaw members 42 and 44 relative to one another.

Figure 5:
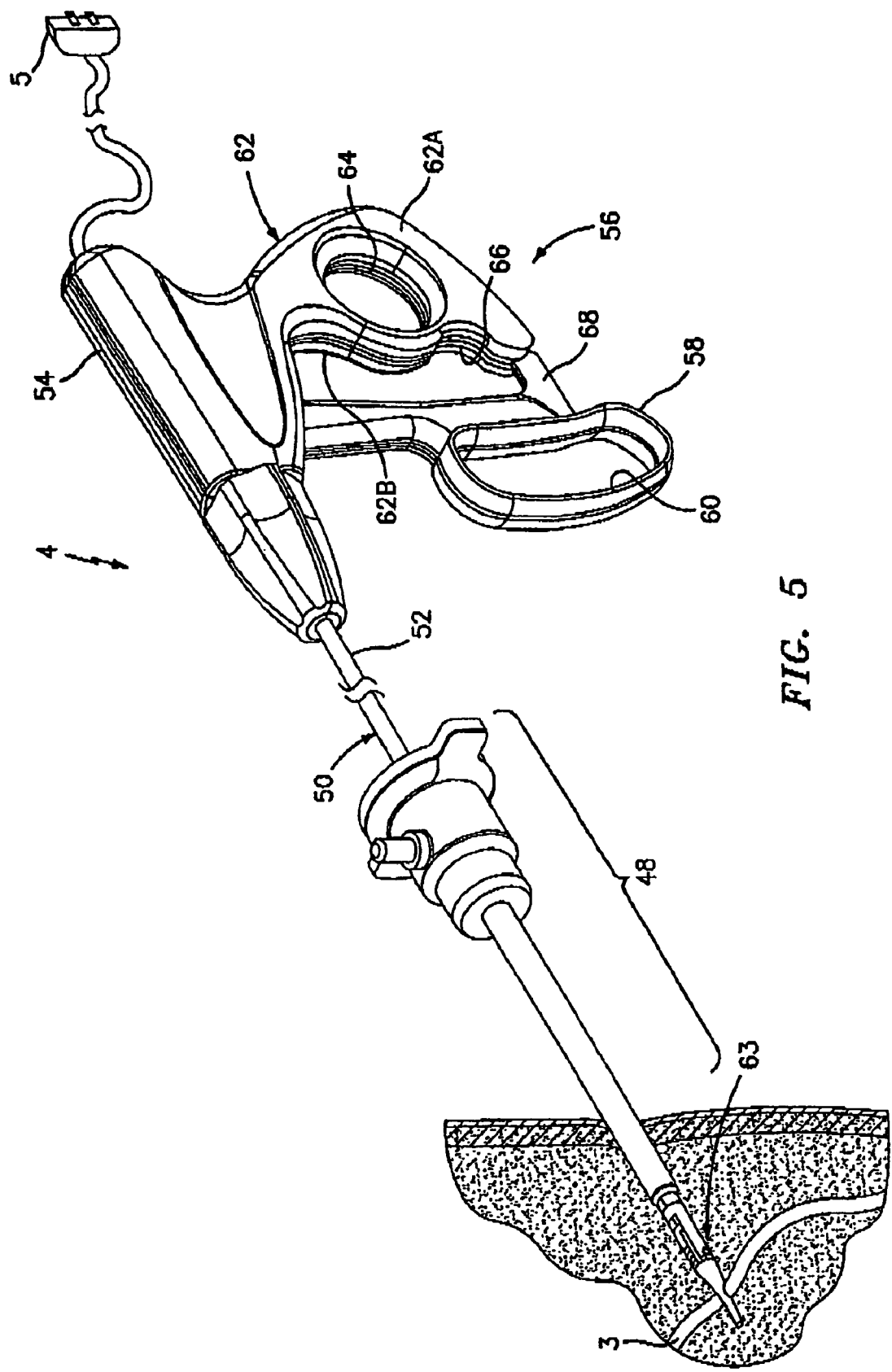
FIG. 5 is a perspective view of an embodiment of a surgical instrument having forceps that are suitable for use in an endoscopic surgical procedure utilizing the electrosurgical system disclosed herein.

FIG. 5 is a perspective view of an embodiment of the surgical instrument 4 having end effector members or forceps 6B that are suitable for an endoscopic surgical procedure. The end effector member 6B is depicted as sealing the tubular vessel 3 through a cannula assembly 130, 132.

The surgical instrument 4 for use with endoscopic surgical procedures includes a drive rod assembly 50 which is coupled to a handle assembly 54. The drive rod assembly 50 includes an elongated hollow shaft portion 52 having a proximal end and a distal end. An end effector assembly 68 is attached to the distal end of shaft 52 and includes a pair of opposing jaw members. Preferably, handle assembly 54 is attached to the proximal end of shaft 52 and includes an activator 56 for imparting movement of the forceps jaw members of end effector member 6B from an open position, wherein the jaw members are disposed in spaced relation relative to one another, to a clamping or closed position, wherein the jaw members cooperate to grasp tissue therebetween.

Activator 56 includes a movable handle 58 having an aperture 60 defined therein for receiving at least one of the operator's fingers and a fixed handle 62 having an aperture 64 defined therein for receiving an operator's thumb. Movable handle 58 is selectively moveable from a first position relative to fixed handle 62 to a second position in the fixed handle 62 to close the jaw members. Preferably, fixed handle 62 includes a channel 66 which extends proximally for receiving a ratchet 68 which is coupled to movable handle 58. This structure allows for progressive closure of the end effector assembly, as well as a locking engagement of the opposing jaw members. In some cases it may be preferable to include other mechanisms to control and/or limit the movement of handle 58 relative to handle 62 such as, e.g., hydraulic, semi-hydraulic and/or gearing systems. As with instrument 4, a stop can also be provided to maintain a preferred gap between the jaw members.

The handle 62 includes handle sections 62a and 62b, and is generally hollow such that a cavity is formed therein for housing various internal components. For example, the cavity can house a PC board which connects the electrosurgical energy being transmitted from the electrosurgical generator 2 to each jaw member, via connector 5. More particularly, electrosurgical energy generated from the electrosurgical generator 2 is transmitted to the handle PC board by a cable 5A. The PC board diverts the electrosurgical energy from the generator into two different electrical potentials which are transmitted to each jaw member by a separate terminal clip. The handle 62 may also house circuitry that communicates with the generator 2, for example, identifying characteristics of the electrosurgical tool 4 for use by the electrosurgical generator 2, where the electrosurgical generator 2 may select a particular seal parameter lookup table based on those characteristics (as described below).

Preferably, a lost motion mechanism is positioned between each of the handle sections 62a and 62b for maintaining a predetermined or maximum clamping force for sealing tissue between the jaw members.

Having thus described two exemplary and non-limiting embodiments of surgical instruments 4 that can be employed with the electrosurgical generator 2, a description will now be provided of various aspects of the inventive electrosurgical generator 2.

Figures 6A, 6B:
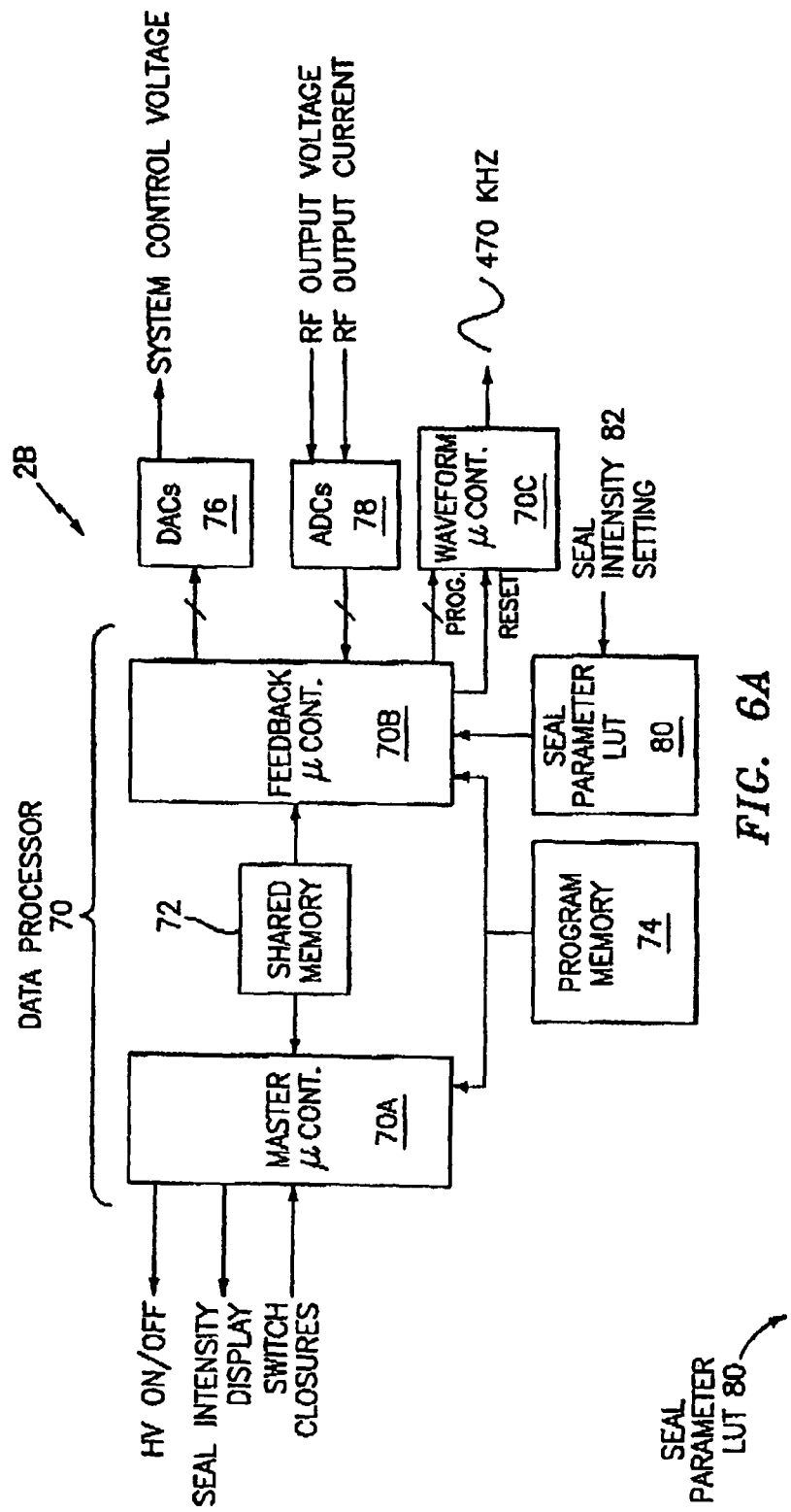
FIG. 6A is a simplified block diagram of a presently preferred embodiment of the power control circuit of the electrosurgical generator of FIG. 2.
FIG. 6B depicts the organization of a seal parameter lookup table (LUT) shown in FIG. 6A.

FIG. 6A is a block diagram that illustrates the power control circuit 2B of FIG. 2 in greater detail. The power control circuit 2B includes a suitably programed data processor 70 that is preferably implemented as one or more microcontroller devices. In a most preferred embodiment there are two principal microcontrollers, referred to as a main microcontroller 70A and a feedback microcontroller 70B. These two microcontrollers are capable of communicating using shared data that is stored and retrieved from a shared read/write memory 72. A control program for the data processor 70 is stored in a program memory 74, and includes software routines and algorithms for controlling the overall operation of the electrosurgical generator 2. In general, the feedback microcontroller 70B has a digital output bus coupled to an input of a digital to analog converter (DAC) block 76 which outputs an analog signal. This is a system control voltage (SCV), which is applied to the variable DC power supply 2C to control the magnitude of the voltage and current of output RF pulses.

An analog to digital converter (ADC) block 78 receives analog inputs and sources a digital input bus of the feedback microcontroller 70B, using the ADC block 78 the microcontroller 70B is apprised of the value of the actual output voltage and the actual output current, thereby closing the feedback loop with the SCV signal. The values of the output voltage and current can be used for determining tissue impedance, power and energy delivery for the overall, general control of the applied RF energy waveform. It should be noted that at least the ADC block 78 can be an internal block of the feedback microcontroller 70B, and need not be a separate, external component. It should be further noted that the same analog signals can be digitized and read into the master microcontroller 70A, thereby providing redundancy. The master microcontroller 70A controls the state (on/off) of the high voltage (e.g., 190V max) power supply as a safety precaution, controls the front panel display(s), such as a Seal Intensity display, described below and shown in FIG. 9A, and also receives various input switch closures, such as a Seal Intensity selected by an operator.

It is noted that in a preferred embodiment of the electrosurgical generator 2 a third (waveform) microcontroller 70C is employed to generate the desired 470 kHz sinusoidal waveform that forms the basis of the RF pulses applied to the tissue to be sealed, such as the vessel 3 (FIG. 2). The waveform microcontroller 70C is controlled by the feedback microcontroller 70B and is programmed thereby. An output signal line from the feedback microcontroller 70B is coupled to a Reset input of the waveform microcontroller 70C to essentially turn the waveform microcontroller 70C on and off to provide the pulsed RF signal in accordance with an aspect of this disclosure. This particular arrangement is, of course, not to be viewed in a limiting sense upon the practice of this system, as those skilled in the art may derive a number of methods and circuits for generating the desired RF pulses in accordance with the teachings found herein.

As an overview, the software algorithms executed by the data processor 70 provide the following features. First, and referring now also to the preferred waveform depicted in FIG. 7, a low power initial pulse of RF energy is used to sense at least one electrical characteristic of the tissue prior to starting the seal cycle. Second, the sensed electrical characteristic of the tissue is used as an input into the determination of the initial sealing parameters, thereby making the sealing procedure adaptive to the characteristics of the tissue to be sealed. Third, the technique measures the time required for the tissue to begin desiccating, preferably by observing an electrical transient, to determine and/or modify further seal parameters. Fourth, the technique performs a tissue temperature control function by adjusting the duty cycle of RF pulses applied to the tissue, thereby avoiding excessive tissue heating and the problems that arise from excessive tissue heating. This is preferably accomplished by using at least one calculated seal parameter related to the time required for the tissue to begin desiccating. Fifth, the technique controllably changes the RF pulse voltage with each pulse of RF energy DEL as the tissue desiccates and shrinks (thereby reducing the pacing between the surgical instrument electrodes), arcing between the instrument electrodes (e.g. 21A and 21B of FIG. 4) is avoided, as is the tissue destruction that may result from such uncontrolled arcing This is also preferably accomplished by using at least one calculated seal parameter that is related to the time required for the tissue to begin desiccating. Sixth, the above-mentioned Seal Intensity front panel control (FIG. 9A) enables the operator to control the sealing of tissue by varying parameters other than simply the RF power. These various aspects of this disclosure are now described in further detail.

Figure 13:
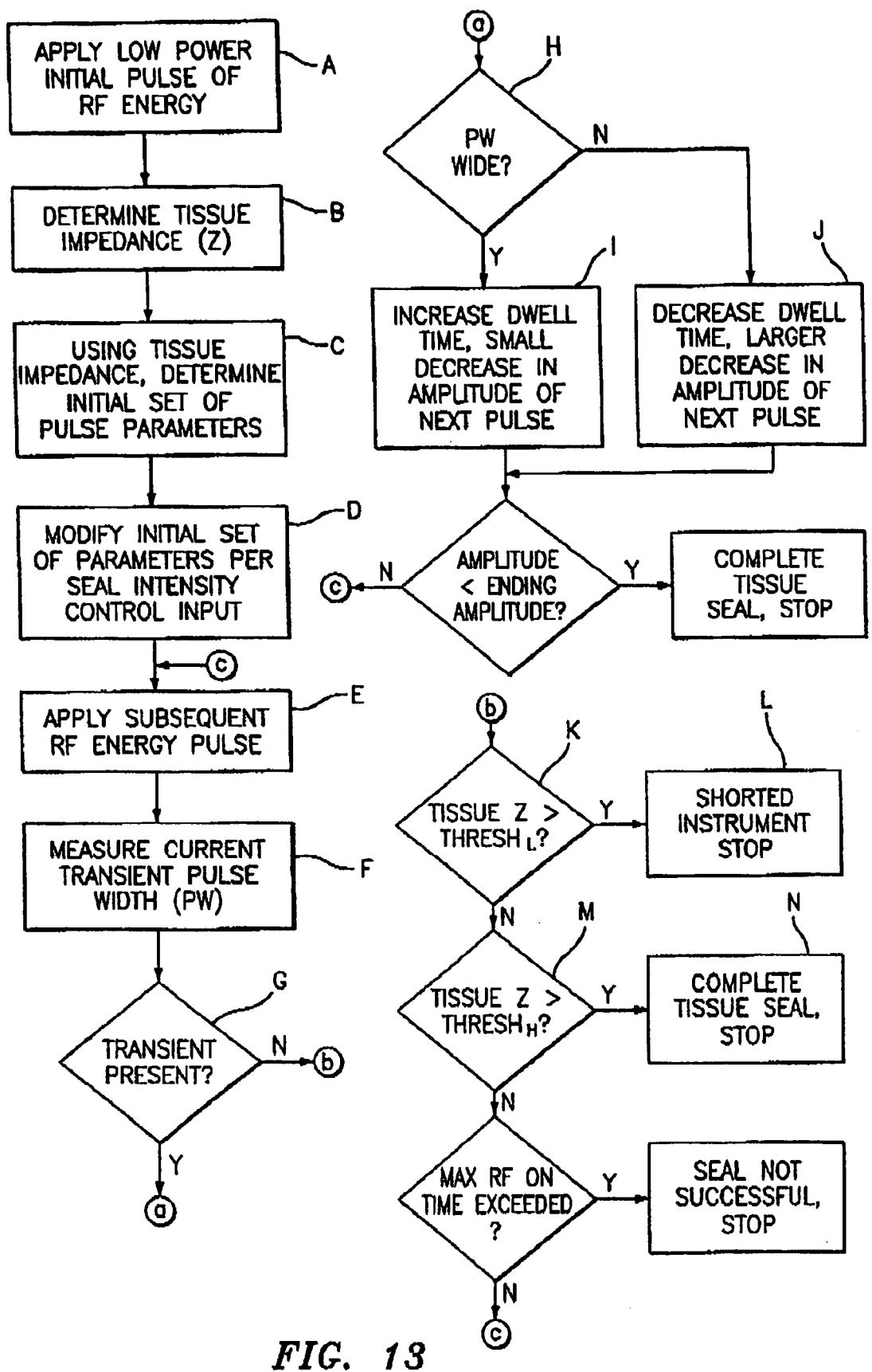
FIG. 13 is a more detailed logic flow diagram that illustrates a method in accordance with the system disclosed herein.

Referring now also to the logic flow diagram of FIG. 13, the impedance sensing feature is implemented at the beginning of the seal cycle, wherein the electrosurgical generator 2 senses at least one electrical characteristic of the tissue, for example, impedance, I-V phase rotation, or the output current, by using a short burst of RF energy (FIG. 13, Steps A and B). The electrical characteristic of the tissue may be measured at any frequency or power level, but preferably is performed at the same frequency as the intended working frequency (e.g., 470 kHz). In a most preferred case the short burst of RF energy (preferably less than about 200 millisecond, and more preferably about 100 millisecond) is a 470 kHz sine wave with approximately 5 W of power. The initial pulse RF power is made low, and the pulse time is made as short as possible, to enable an initial tissue electrical characteristic measurement to be made without excessively heating the tissue.

In a most preferred embodiment the electrical characteristic sensed is the tissue impedance which is employed to determine an initial set of parameters that are input to the sealing algorithm, and which are used to control the selection of sealing parameters, including the starting power, current and voltage (FIG. 13, Step C). Other sealing parameters may include duty cycle and pulse width. Generally, if the sensed impedance is in the lower ranges, then the initial power and starting voltage are made relatively lower, the assumption being that the tissue will desiccate faster and require less energy. If the sensed impedance is in the higher ranges, the initial power and starting voltage are made relatively higher, the assumption being that the tissue will desiccate slower and require more energy.

In other embodiments at least one of any other tissue electrical characteristic, for example, the voltage or current, can be used to set the parameters. These initial parameters are preferably modified in accordance with the setting of the Seal Intensity control input (FIG. 13, Step D), as will be described in further detail below.

Referring again to FIG. 13, Step C, the sensed impedance is employed to determine which set of values are used from a seal parameter lookup table (LUT) 80 (see FIGS. 6A and 6B). The seal parameter look up table may one of a plurality that are stored in the generator or accessible to the generator. Furthermore, the seal parameter table may be selected manually or automatically, based on, for example, the electrosurgical tool or instrument being employed. The specific values read from the seal parameter LUT 80 (FIG. 6B) are then adjusted based on the Seal Intensity front panel setting 82 (FIG. 13, Step D), as is shown more clearly in FIGS. 9A and 9B. In a preferred, but not limiting embodiment, the values read from the seal parameter LUT 80 comprise the power, the maximum voltage, starting voltage, minimum voltage, voltage decay, voltage ramp, maximum RF on time, maximum cool scale factor, pulse minimum, pulse dwell time, pulse off time, current and the desired pulse width. In a preferred, but not limiting embodiment, the seal parameter values adjusted by the Seal Intensity front panel setting 82 (FIGS. 9A and 9B) comprise the power, starting voltage, voltage decay, and pulse dwell time.

Figure 1B:
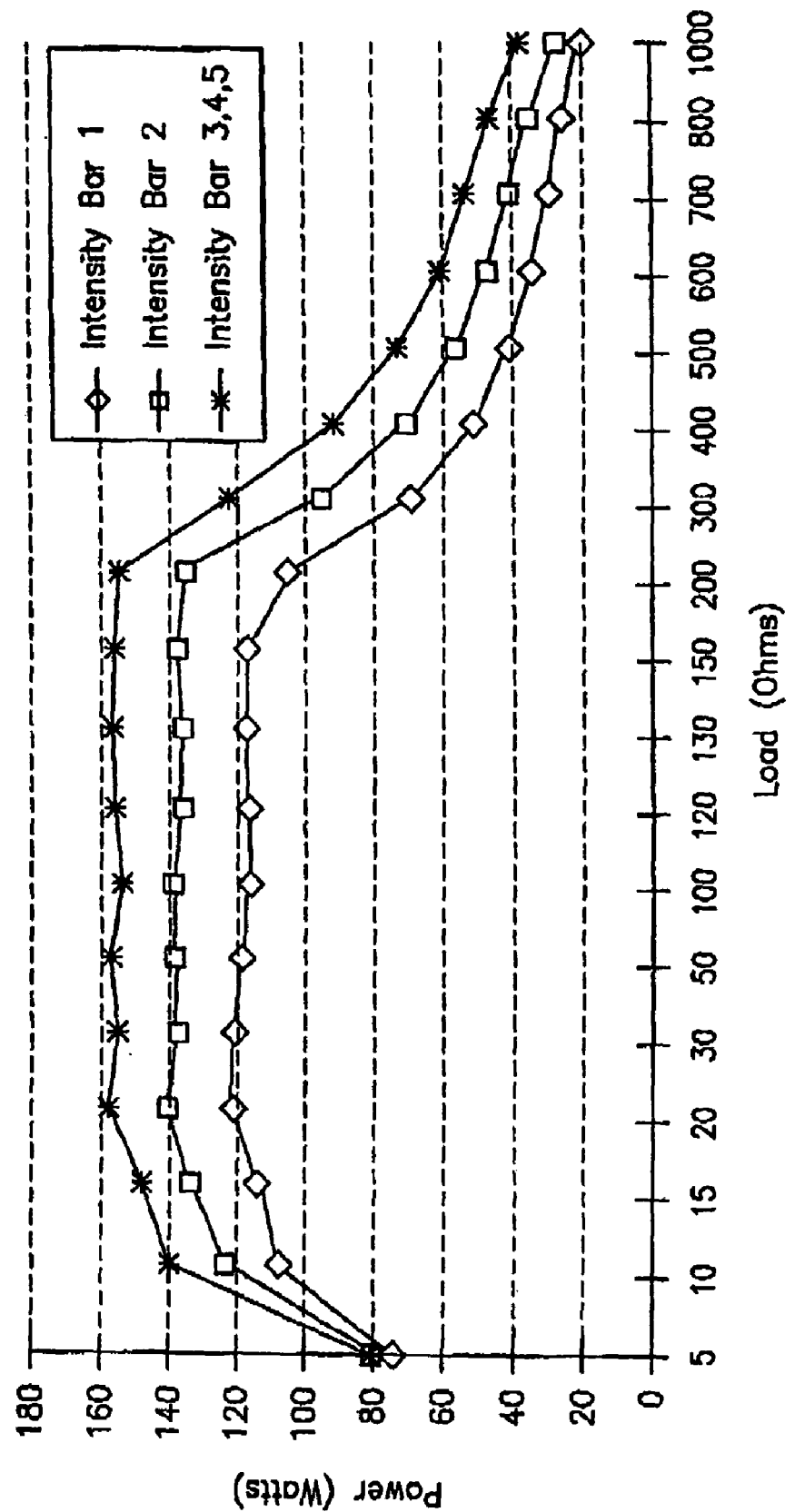
FIG. 1B is a graph that plots output power versus impedance in ohms, in accordance with the operation of an electrosurgical generator that is an aspect of this disclosure.
Figure 9:
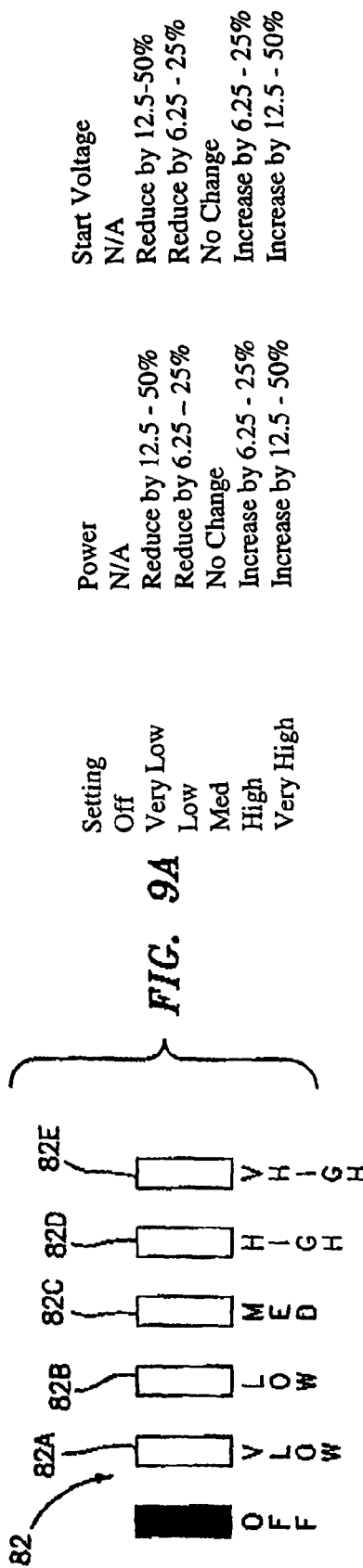

FIG. 1B is a graph that plots output power versus impedance in ohms for the disclosed electrosurgical generator. The plot labeled "Intensity Bar 1" shows the electrosurgical generator power output versus impedance when the "VLOW" setting 82A (FIG. 9A) of the Seal Intensity front panel setting 82 is selected. The plot labeled Intensity Bar 2 shows the power output of the electrosurgical generator when the "LOW" setting 82B of the Seal Intensity front panel setting 82 is selected. The plot labeled Intensity Bars 3, 4, 5, shows the power output of the electrosurgical generator when the "MED" 82C, "HIGH" 82D or VHIGH" 82E Seal Intensity front panel settings 82 are selected. The Seal Intensity front panel settings 82 adjust the seal parameter values as shown in FIG. 9B. These values may be adjusted depending on instrument used, tissue characteristics or surgical intent.

Figure 7A:
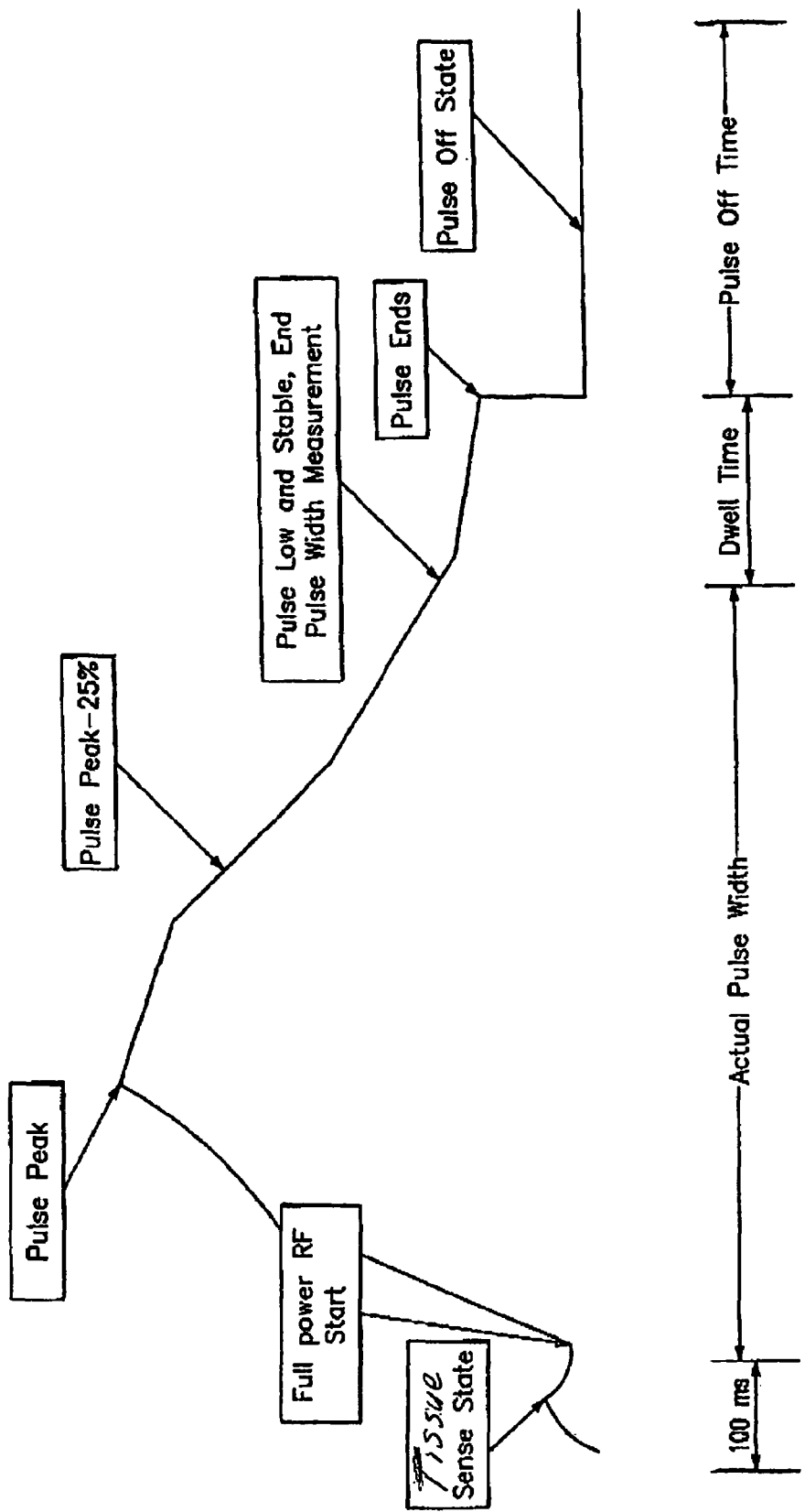
FIGS. 7A and 7B illustrate a presently preferred electrosurgical generator output waveform of RMS current vs. time for implementing at least the first pulse of the pulsed operation mode that is an aspect of this disclosure.
Figure 7B:
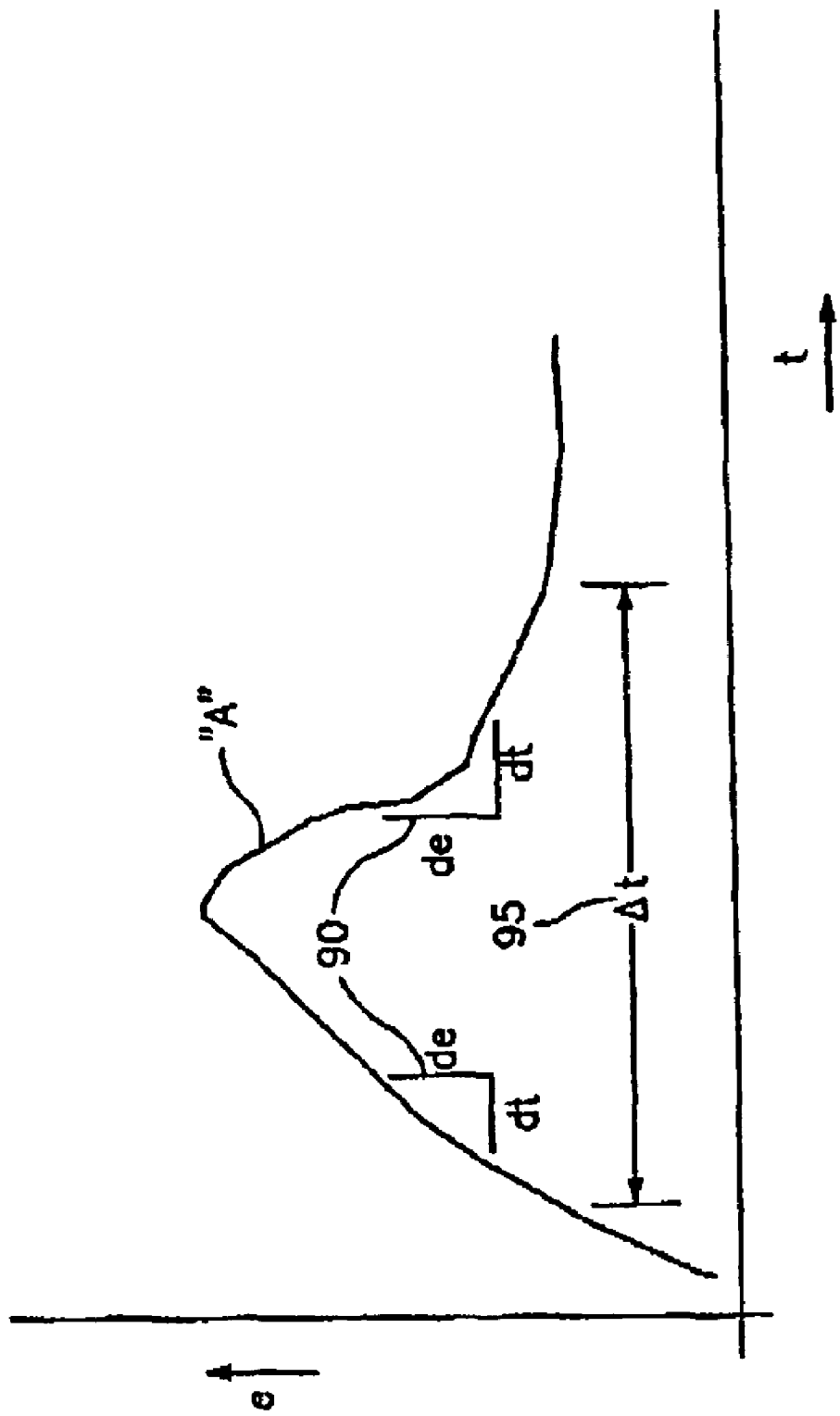
Figure 8:
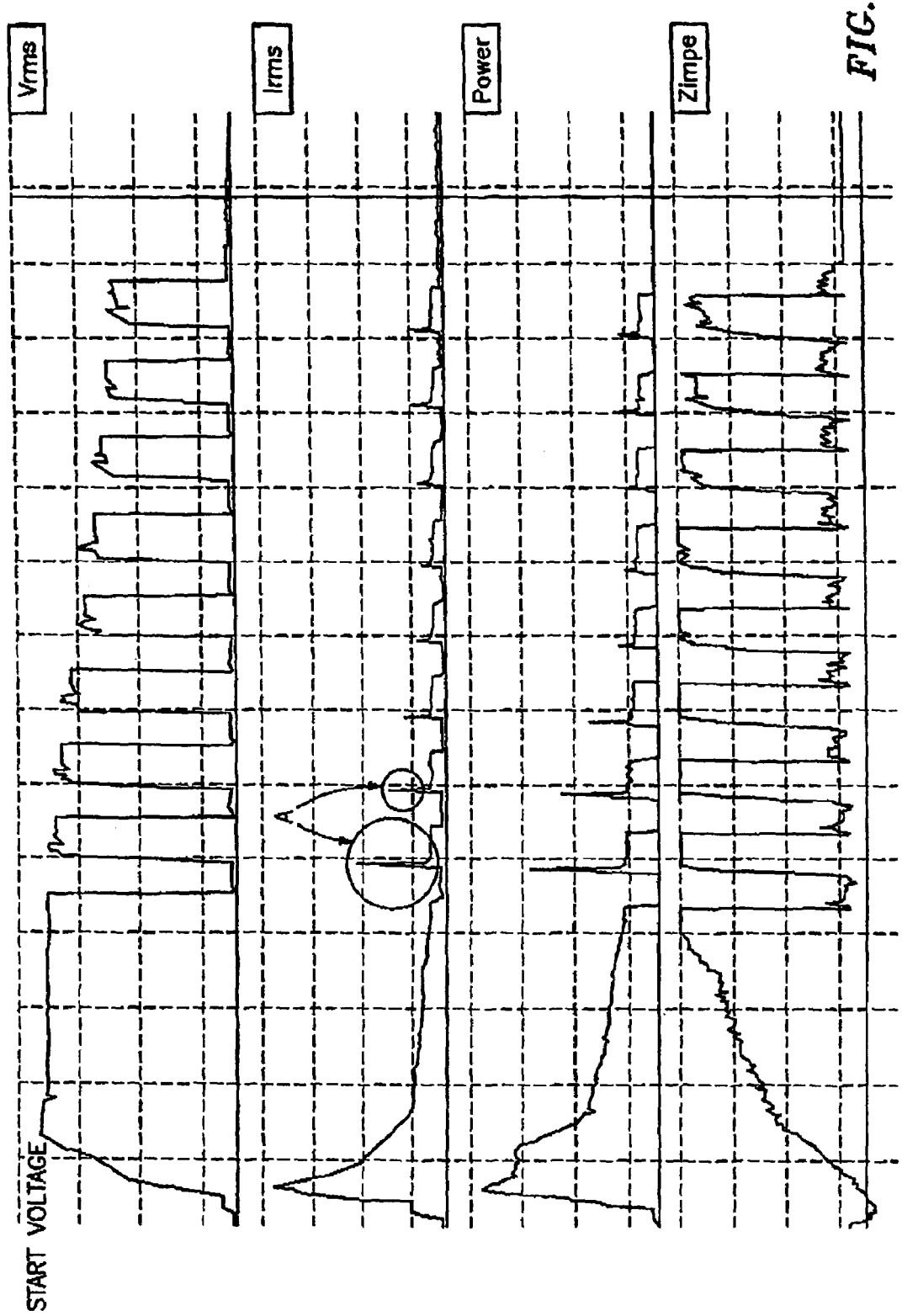
FIG. 8 depicts a full set of electrosurgical RF pulses in accordance with this disclosure, and illustrates the voltage, current and power characteristics of the pulses, as well as the response of the tissue impedance to the applied RF pulses.

Discussing this aspect of the disclosure now in further detail, and referring as well to FIGS. 7 and 8, the selected Seal Parameter Table, adjusted by the Seal Intensity front panel settings is then utilized by the RF energy generation system and an initial RF sealing pulse is then started.

As each pulse of RF energy is applied to the tissue, the current initially rises to a maximum (Pulse Peak) and then, as the tissue desiccates and the impedance rises due to loss of moisture in the tissue, the current falls. Reference in this regard can be had to the circled areas designated as "A" in the $I_{rms}$ waveform of FIG. 8. The actual width of the resulting electrical transient, preferably a current transient "A", is an important factor in determining what type and amount of tissue is between the jaws (electrodes) of the surgical instrument 4 (measured from "Full Power RF Start" to "Pulse Low and Stable".) The actual current transient or pulse width is also employed to determine the changes to, or the values of, the parameters of the pulse duty cycle ("Dwell Time") and to the change of the pulse voltage, as well as other parameters. This parameter can also be used to determine whether the tissue seal has been completed, or if the surgical instrument 4 has shorted.

As an alternative to directly measuring the pulse width, the rate of change of an electrical characteristic (for example current, voltage, impedance, etc.) of the transient "A" (shown in FIG. 7B) may be measured periodically (indicated by the reference number 90 shown in FIG. 7B) over the time the transient occurs. The rate of change of the electrical characteristic may be proportional to the width Δt 95 of the transient "A", defined by the relationship:

$$\Delta t \propto de/dt$$

where de/dt is the change in the electrical characteristic over time. This rate of change may then be used to provide an indication of the width of the transient "A" in determining the type and amount of tissue that is between the jaws (electrodes) of the surgical instrument 4, as well as the subsequent pulse duty cycle ("Dwell Time"), the amount of subsequent pulse voltage reduction, as well as other parameters.

Referring to FIG. 13, Step E, a subsequent RF energy pulse is applied to the tissue, and the pulse width of the leading edge current transient is measured (FIG. 13, Step F). A determination is made if the current transient is present. If it is, control passes via connector "a" to Step H, otherwise control passes via connector "b" to Step K.

Assuming that the current transient is present, and referring to FIG. 13, Step H, if the current transient pulse is wide, for example, approximately in the range of 500-1000 ms, then one can assume the presence of a large amount of tissue, or tissue that requires more RF energy to desiccate. Thus, the Dwell Time is increased, and an increase or small reduction is made in the amplitude of the next RF pulse (see the Vrms waveform in FIG. 8, and FIG. 13, Step I). If the current transient pulse is narrow, for example, about 250 ms or less (indicating that the tissue impedance rapidly rose), then one can assume a small amount of tissue, or a tissue type that requires little RF energy to desiccate is present. Other ranges of current transient pulse widths can also be used. The relationship between the current transient pulse width and the tissue characteristics may be empirically derived. In this case the Dwell Time can be made shorter, and a larger reduction in the amplitude of the next RF pulse can be made as well (FIG. 13, Step J).

If a current pulse is not observed at FIG. 13, Step G, it may be assumed that either the instrument 4 has shorted, the tissue has not yet begun to desiccate, or that the tissue has been fully desiccated and, thus, the seal cycle is complete. The determination of which of the above has occurred is preferably made by observing the tissue impedance at FIG. 13, Steps K and M. If the impedance is less than a low threshold value (THRESH$_L$), then a shorted instrument 4 is assumed (FIG. 13, Step L), while if the impedance is greater than a high threshold value (THRESH$_H$), then a complete tissue seal is assumed (FIG. 13, Step N).

If the tissue impedance is otherwise found to be between the high and low threshold values, a determination is made as to whether the Max RF On Time has been exceeded. If the Max RF On Time has been exceeded, it is assumed that the seal cannot be successfully completed for some reason and the sealing procedure is terminated. If the Max RF On Time has not been exceeded then it is assumed that the tissue has not yet received enough RF energy to start desiccation, and the seal cycle continues (connector "c").

After the actual pulse width measurement has been completed, the Dwell Time is determined based on the actual pulse width and on the Dwell Time field in the seal parameter LUT 80 (see FIG. 6B.) The RF pulse is continued until the Dwell Time has elapsed, effectively determining the total time that RF energy is delivered for that pulse. The RF pulse is then turned off or reduced to a very low level for an amount of time specified by the Pulse Off field. This low level allows some moisture to return to the tissue.

Based on the initial Desired Pulse Width field of the seal parameter LUT 80 for the first pulse, or, for subsequent pulses, the actual pulse width of the previous pulse, the desired voltage limit kept constant or adjusted based on the Voltage Decay and Voltage Ramp fields. The desired voltage limit Is kept constant or raised during the pulse if the actual pulse width is greater than the Desired Pulse Width field (or last actual) pulse width), and is kept constant or lowered if the actual pulse width is less than the Desired Pulse Width field (or the last actual pulse width).

When the Desired Voltage has been reduced to the Minimum Voltage field, then the RF energy pulsing is terminated and the electrosurgical generator 2 enters a cool-down period having a duration that is set by the Maximum Cool SF field and the actual pulse width of the first pulse.

Several of the foregoing and other terms are defined with greater specificity as follows (see also FIG. 7).

The Actual Pulse width is the time from pulse start to pulse low. The Pulse Peak is the point where the current reaches a maximum value, and does not exceed this value for some predetermined period of time (measured in milliseconds). The peak value of the Pulse Peak can be reached until the Pulse Peak-X % value is reached, which is the point where the current has decreased to some predetermined determined percentage, X, of the value of Pulse Peak. Pulse Low is the point where the current reaches a low point, and does not go lower for another predetermined period of time. The value of the Maximum RF On Time or MAX Pulse Time is preferably preprogrammed to some value that cannot be readily changed. The RF pulse is terminated automatically if the Pulse Peak is reached but the Pulse Peak-X% value is not obtained with the duration set by the Maximum RF On Time field of the seal parameter LUT 80.

Referring to FIG. 6B, the seal parameter LUT 80 is employed by the feedback microcontroller 70B in determining how to set the various outputs that impact the RF output of the electrosurgical generator 2. The seal parameter LUT 80 is partitioned into a plurality of storage regions, each being associated with a particular measured initial impedance. More particularly, the Impedance Range defines a plurality of impedance breakpoints (in ohms) which are employed to determine which set of variables are to be used for a particular sealing cycle. The particular Impedance Range that is selected is based on the above described Impedance Sense State (FIG. 7) that is executed at the start of the seal cycle. The individual data fields of the seal parameter LUT 80 are defined as follows.

The actual values for the Impedance Ranges of Low, Med Low, Med High, or High, are preferably contained in one of a plurality of tables stored in the generator 2, or otherwise accessible to the generator 2. A specific table may be selected automatically, for example, based on signals received from the electrosurgical tool 4 being used, or by the operator indicating what electrosurgical tool is in use.

Power is the RF power setting to be used (in Watts). Max Voltage is the greatest value that the output voltage can achieve (e.g., range 0-about 190V). Start Voltage is the greatest value that the first pulse voltage can achieve (e.g., range 0-about 190V). Subsequent pulse voltage values are typically modified downwards from this value. The Minimum Voltage is the voltage endpoint, and the seal cycle can be assumed to be complete when the RF pulse voltage has been reduced to this value, The Voltage Decay scale factor is the rate (in volts) at which the desired voltage is lowered if the current Actual Pulse Width is less than the Desired Pulse Width. The Voltage Ramp scale factor is the rate at which the desired voltage will be increased if the Actual Pulse Width is greater than the Desired Pulse Width. The Maximum RF On Time is the maximum amount of time (e.g., about 5-20 seconds) that the RF power can be delivered, as described above. The Maximum Cool Down Time determines the generator cool down time, also as described above. Pulse Minimum establishes the minimum Desired Pulse Width value. It can be noted that for each RF pulse, the Desired. Pulse Width is equal to the Actual Pulse Width from the previous pulse, or the Desired Pulse field if the first pulse. The Dwell Time scale factor was also discussed previously, and is the time (in milliseconds) that the RF pulse is continued after the current drops to the Pulse Low and Stable point (see FIG. 7). Pulse Off is the off time (in milliseconds) between RF pulses. Desired Pulse Width is a targeted pulse width and determines when the Desired Voltage (Vset) is raised, lowered or kept constant. If the Actual Pulse Width is less than the Desired Pulse Width, then Vset is decreased, while if the Actual Pulse Width is greater than the Desired Pulse Width, then Vset is increased. If the Actual Pulse Width is equal to the Desired Pulse Width, then Vset is kept constant. The Desired Pulse Width is used as the Desired Pulse Width for each sequential pulse. In general, a new Desired Pulse Width cannot be greater than a previous Desired Pulse Width, and cannot be less than Pulse Minimum.

By applying the series of RF pulses to the tissue, the surgical generator 2 effectively raises the tissue temperature to a certain level, and then maintains the temperature relatively constant. If the RF pulse width is too long, then the tissue may be excessively heated and may stick to the electrodes 21A, 21B of the surgical instrument 4, and/or an explosive vaporization of tissue fluid may damage the tissue, such as the vessel 3. If the RF pulse width is too narrow, then the tissue will not reach a temperature that is high enough to properly seal. As such, it can be appreciated that a proper balance of duty cycle to tissue type is important.

During the pulse off cycle that is made possible in accordance with the teachings herein, the tissue relaxes, thereby allowing the steam to exit without tissue destruction. The tissue responds by rehydrating, which in turn lowers the tissue impedance. The lower impedance allows the delivery of more current in the next pulse. This type of pulsed operation thus tends to regulate the tissue temperature so that the temperature does not rise to an undesirable level, while still performing the desired electrosurgical procedure, and may also allow more energy to be delivered, and thus achieving better desiccation.

As each RF pulse is delivered to the tissue, the tissue desiccates and shrinks due to pressure being applied by the jaws of the surgical instrument 4. The inventors have realized that if the voltage applied to the tissue is not reduced, then as the spacing between the jaws of the surgical instrument 4 is gradually reduced due to shrinking of the tissue, an undesirable arcing can develop which may vaporize the tissue, resulting in bleeding.

As is made evident in the $V_{rms}$ trace of FIG. 8, and as was described above, the voltage of each successive RF pulse can be controllably decreased, thereby compensating for the desiccation-induced narrowing of the gap between the surgical instrument electrodes 21A and 21B. That is, the difference in electric potential between the electrodes is decreased as the gap between the electrodes decreases, thereby avoiding arcing.

As was noted previously, the Seal Intensity front panel adjustment is not a simple RF power control. The adjustment of the seal intensity is accomplished by adjusting the power of the electrosurgical generator 2, as well as the generator voltage, the duty cycle of the RF pulses, the length of time of the seal cycle (e.g., number of RF pulses), and the rate of voltage reduction for successive RF pulses. FIGS. 9B and 9C illustrate an exemplary set of parameters (Power, Start Voltage, Voltage Decay and Dwell Time), and how they modify the contents of the seal parameter LUT 80 depending on the setting of the Seal Intensity control 82 shown in FIG. 9A. Generally, higher settings of the Seal Intensity control 82 increase the seal time and the energy delivered while lower settings decrease the seal time and the energy delivered.

In the FIG. 9B embodiment, it is instinctive to note that for the Medium, High and Very High Seal Intensity settings the RF Power remains unchanged, while variations are made instead in the Start Voltage, Voltage Decay and Dwell Time parameters.

Figure 12:
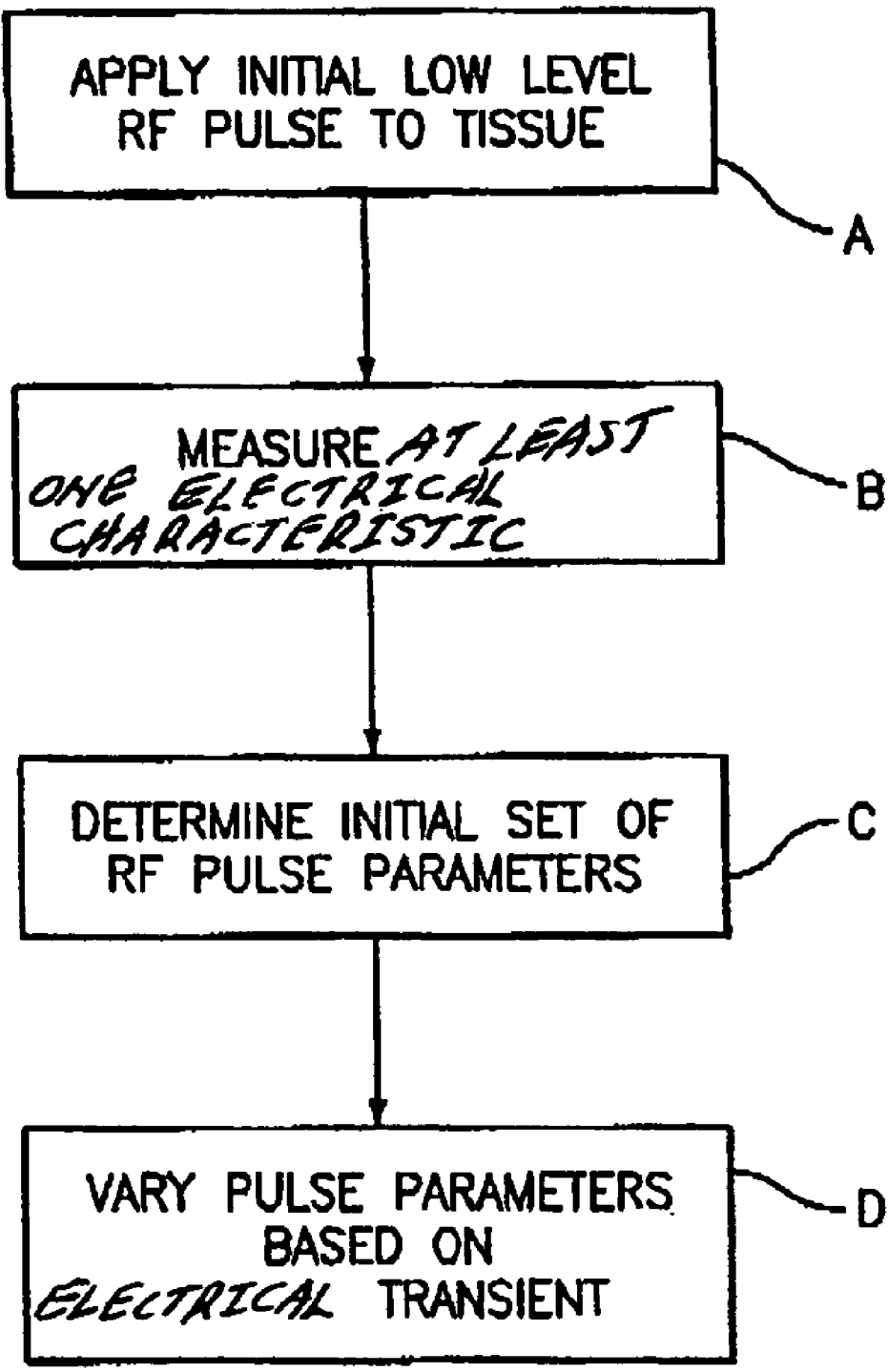
FIG. 12 is a logic flow diagram that illustrates a method in accordance with the system disclosed herein.

Based on the foregoing it can be appreciated that an aspect of this disclosure is a method for electrosurgically sealing a tissue. Referring to FIG. 12, the method includes steps of: (A) applying an initial pulse of RF energy to the tissue, the pulse having characteristics selected so as not to excessively heat the tissue; (B) measuring at least one electrical characteristic of the tissue in response to the applied pulse; (C) in accordance with the measured electrical characteristic, determining an initial set of pulse parameters for use during a first RF energy pulse that is applied to the tissue; and (D) varying the pulse parameters of individual ones of subsequent RF energy pulses in accordance with at least one characteristic of an electric current transient that occurs at the beginning of each individual one (pulses) of the subsequent RF energy pulses. The method can terminate the generation of subsequent RF energy pulses upon a determination that the current transient is absent or that the voltage has been reduced to a predefined level. In another embodiment of the present invention, the initial pulse may be combined with at least the first subsequent pulse.

Figure 10:
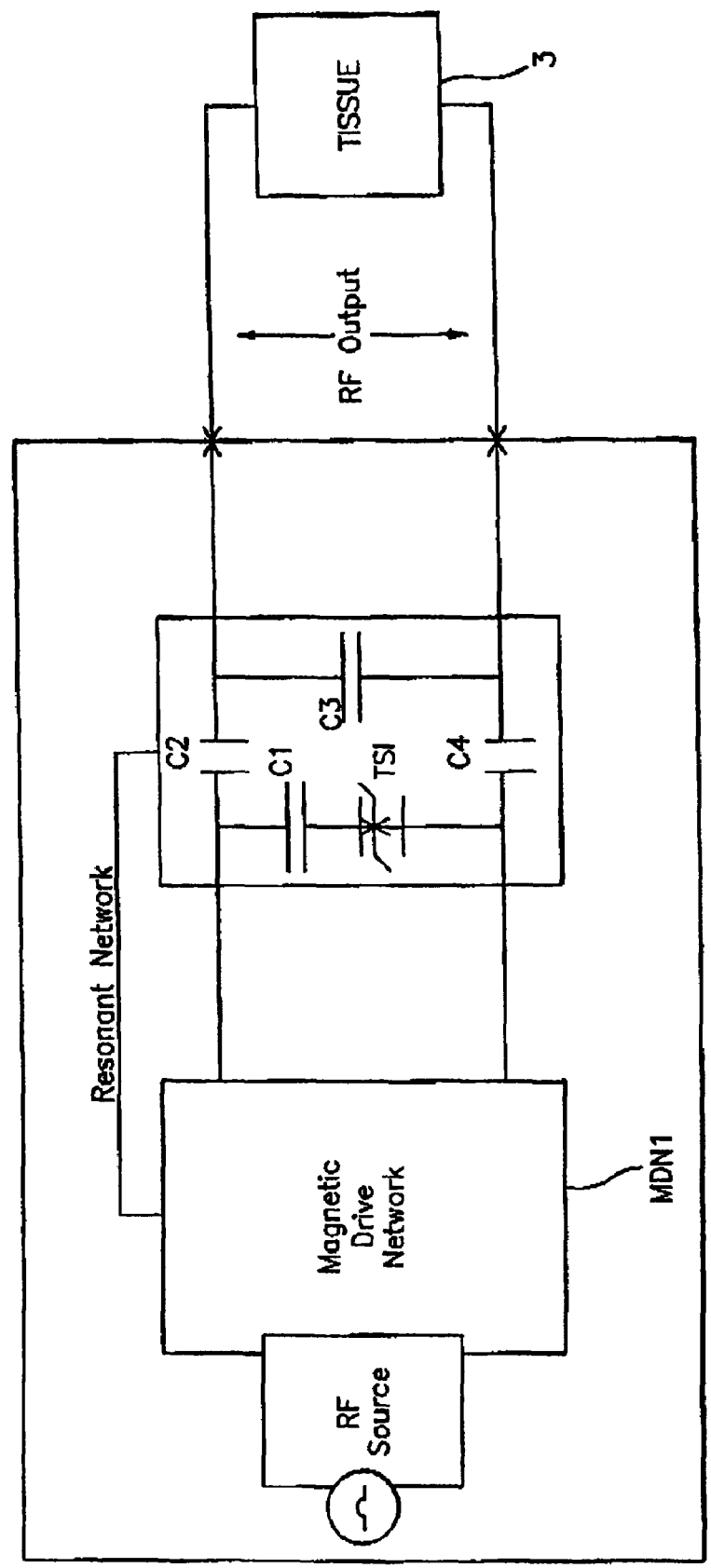
FIG. 10 is a simplified block diagram of a circuit for achieving an overvoltage limiting and transient energy suppression energy function.
Figure 11:
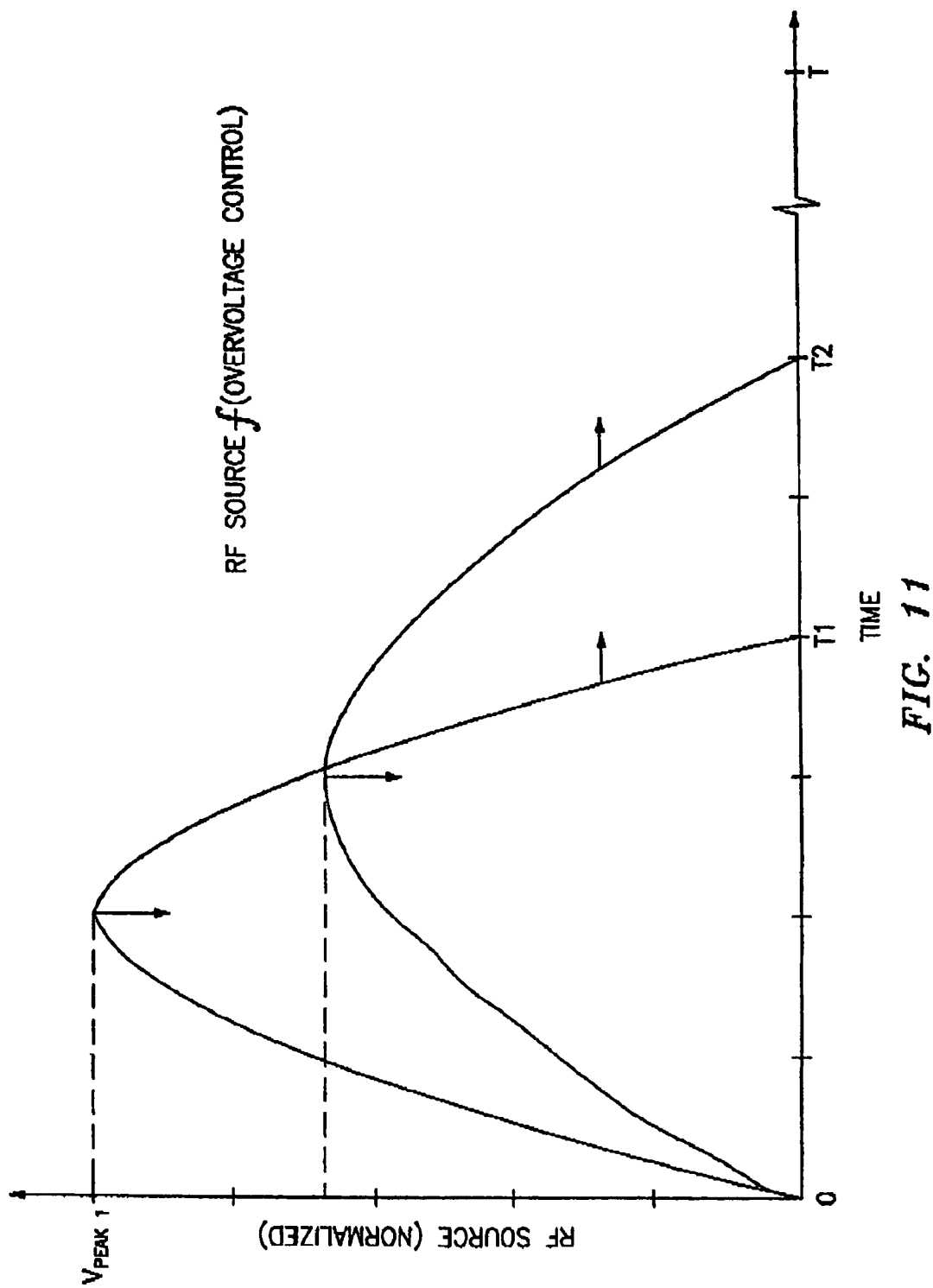
FIG. 11 is a waveform diagram illustrating the effect of the operation of the circuit in FIG. 10.

Reference is now made to FIGS. 10 and 11 for a description of a novel over-voltage limit and transient energy suppression aspect of the system disclosed herein.

A bi-directional transorb TS1 normally is non-operational. As long as the operating RF output levels stay below the turn-on threshold of TS1, electrosurgical energy is provided at a controlled rate of tissue desiccation. However, in the event that rapid tissue desiccation occurs, or that arcing is present in the surgical tissue field, the RF output may exhibit operating voltage levels in excess of the normal RF levels used to achieve the controlled rate of tissue desiccation. If the excess voltage present is left unrestrained, the tissue 3 may begin to exhibit undesirable clinical effects contrary to the desired clinical outcome. The TS1 is a strategic threshold that is set to turn on above normal operating levels, but below and just prior to the RF output reaching an excess voltage level where undesirable tissue effects begin to occur. The voltage applied across TS1 is proportionately scaled to follow the RF output voltage delivered to the tissue 3. The transorb TS1 is selected such that its turn on response is faster than the generator source RF signal. This allows the transorb TS1 to automatically track and respond quickly in the first cycle of an excess RF output overvoltage condition.

Note should be made in FIG. 10 of the capacitor components or network C2, C3, and C4 that parallel the magnetic drive network (MDN1) which has an inductive characteristic and is contained within the electrosurgical generator 2. The combination of the inductive MDN1 and the capacitive networks forms a resonant tuned network which yields the waveshape configuration of the RF source signal shown in FIG. 11.

A turn on of transorb device TS1, which functions as a voltage controlled switch, instantaneously connects the serial capacitance C1 across the capacitor network C2, C3, and C4. An immediate change then appears in the tuning of the resonant network mentioned above, which then instantaneously alters the waveshape of the RF source signal shown in FIG. 11. The time base T1 of the nominally half-sine signal shown increases incrementally in width out to time T2, which automatically lowers the peak voltage of the RF output signal. The peak voltage decreases because the Voltage-Time product of the signal shown in FIG. 11 is constant for a given operating quiescence. The concept of a Voltage-Time product is well known to those skilled in the art, and is not further discussed herein.

As the peak voltage decreases, the excess overvoltage is automatically limited and is restricted to operating levels below that which cause negative clinical effects. Once the excess RF output voltage level falls below the transorb threshold, the TS1 device turns off and the electrosurgical generator 2 returns to a controlled rate of tissue desiccation.

In the event that arcing is present in the surgical tissue field, undesirable excess transient RF energy may exist and may be reflected in the RF output of the electrosurgical generator 2. This in turn may generate a corresponding excess RF output voltage that creates sufficient transient overvoltage to turn on the transorb TS1. In this condition the cycle repeats as described above, where TS1 turns on, alters the resonant tuned network comprised of the magnetic and capacitive components, and thus also alters the RF source signal waveshape. This automatically reduces the excess overvoltage.

In accordance with this aspect of the disclosure, the excess RF transient energy is suppressed and the overvoltage is limited by the dynamic, real-time automatic detuning of the RF energy deliv red to the tissue being treated.

It should be noted that the embodiment of FIGS. 10 and 11 can be used to improve the operation of conventional electrosurgical generators, as well as with the novel pulsed output electrosurgical generator 2 that was described previously.

Figure 14:
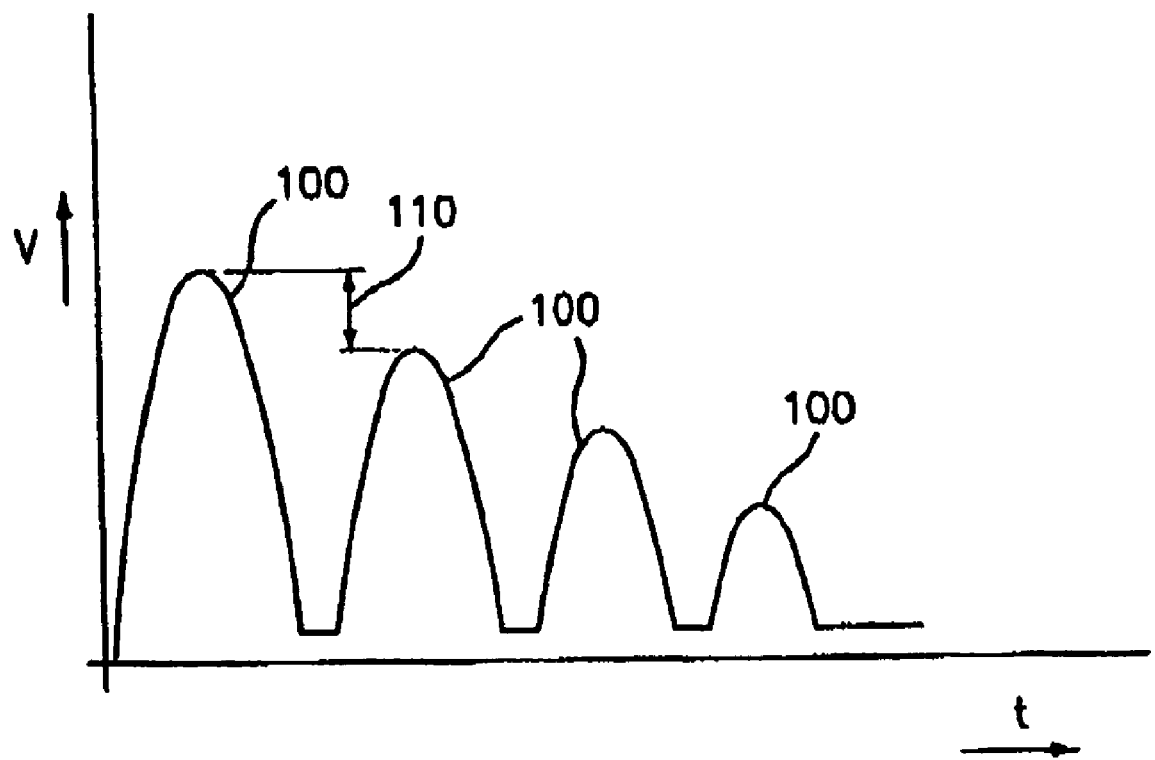
FIG. 14 is a chart illustrating a fixed number of pulses determined from the measured impedance and the RMS current pulse width.

In an additional embodiment the measured electrical characteristic of the tissue, preferably the impedance ($Z_i$) and the RMS current pulse width ($P_w$) may be used to determine a fixed voltage reduction factor ($V_{dec}$) to be used for subsequent pulses, and to determine a fixed number of pulses ($P_F$) to be delivered for the sealing procedure. The relationship among the voltage reduction factor, the measured impedance and the RMS current pulse width may be defined as $V_{dec}=F(Z_i, P_w)$, and the relationship among the number of pulses, the measured impedance and the RMS current pulse width may be defined as $P_F=F'(Z_i, P_w)$. In FIG. 14 a fixed number of pulses, $P_F$, 100 determined from the measured impedance and the RMS current pulse width are shown. Each subsequent pulse may be reduced by the fixed voltage reduction factor ($V_{dec}$) 110, also determined from the measured impedance and the RMS current pulse width.

In a further additional embodiment, tissue sealing is accomplished by the electrosurgical system described above by continuously monitoring or sensing the current or tissue impedance rate of change. If the rate of change increases above a predetermined limit, then RF pulsing is automatically terminated by controlling the electrosurgical generator 2 accordingly and any previously changed pulse parameters (e.g., power, voltage and current increments) are reset to the original default values. In this embodiment, the ending current or tissue impedance, i.e., the current or tissue impedance at the end of each RF pulse, is also continuously monitored or sensed. The ending values are then used to determine the pulse parameters for the subsequent RF pulse; to determine if the seal cycle should end (based on the ending values of the last few RF pulses which did not change by more than a predetermined amount); and to determine the duty cycle of the subsequent RF pulse.

Further, in this embodiment, RF power, pulse width, current and/or voltage levels of subsequent RF pulses can be kept constant or modified on a pulse-by-pulse basis depending on whether the tissue has responded to the previously applied RF energy or pulse (i.e., if the tissue impedance has begun to rise). For example, if the tissue has not responded to a previously applied RF pulse, the RF power output, pulse width, current and/or voltage levels are increased for the subsequent RF pulse.

Hence, since these RF pulse parameters can subsequently be modified following the initial RF pulse, the initial set of RF pulse parameters, i.e., a magnitude of a starting RF power level, a magnitude of a starting voltage level, a magnitude of the starting pulse width, and a magnitude of a starting current level, are selected accordingly such that the first or initial RF pulse does not excessively heat the tissue. One or more of these starting levels are modified during subsequent RF pulses to account for varying tissue properties, if the tissue has not responded to the previously applied RF pulse which includes the initial RF pulse.

The above functions are implemented by a seal intensity algorithm represented as a set of programmable instructions configured for being executed by at least one processing unit of a vessel sealing system. The vessel sealing system includes a Seal Intensity control panel for manually adjusting the starting voltage level, in a similar fashion as described above with reference to FIGS. 9A and 9B.

Figure 15:
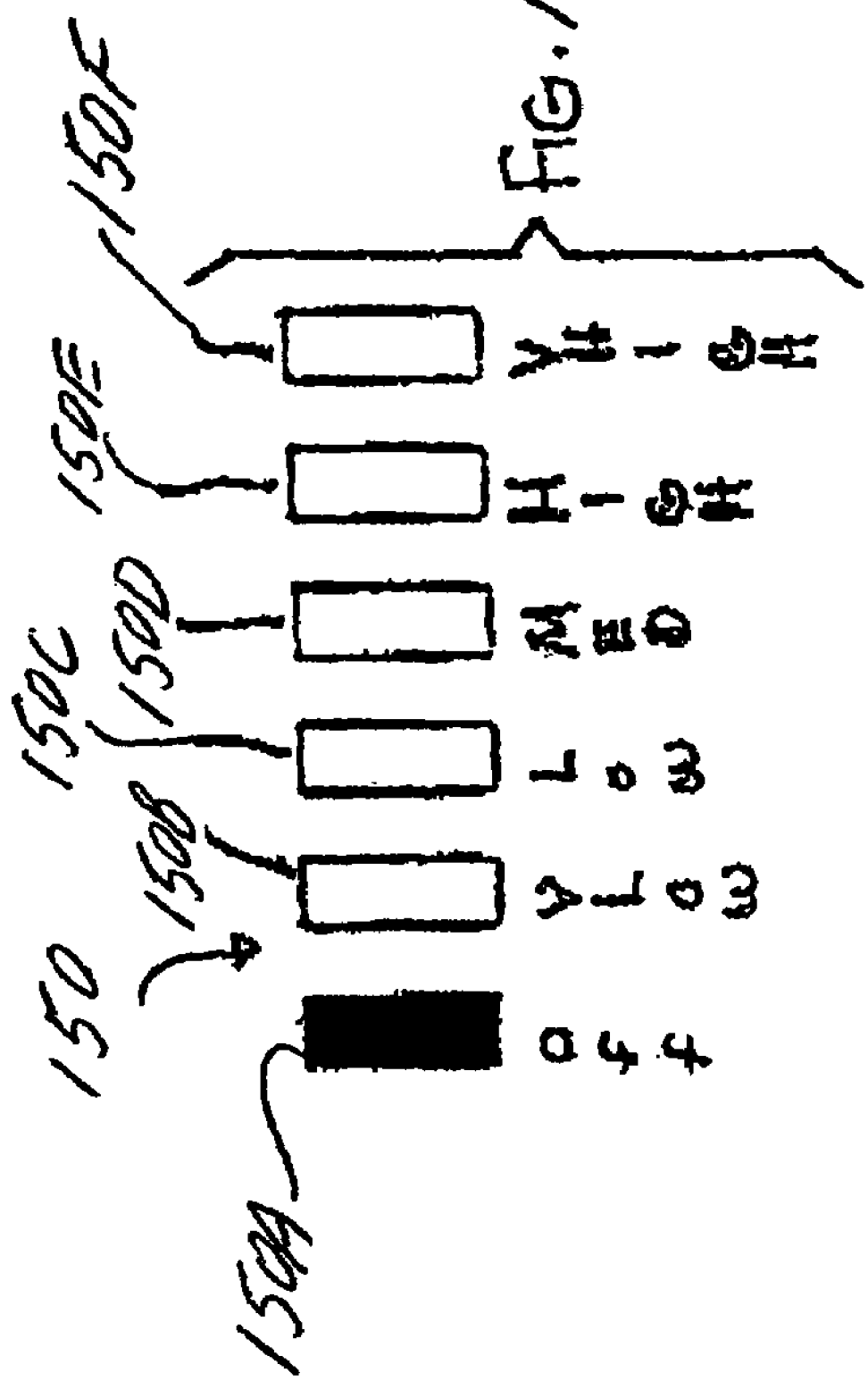
FIG. 15 illustrates a Seal Intensity control that forms a part of this disclosure.

As shown in FIG. 15, a preferred Seal Intensity control panel of the present inventive embodiment includes six settings, i.e., "Off" 150A, "VLOW" 150B, "LOW" 150C, "MED" 150D, "HIGH" 150E and "VHIGH" 150F. The Seal Intensity front panel settings 150 adjust the seal parameter values of the Seal Parameter Table as shown by FIGS. 9B and 9C. The selected Seal Parameter Table, adjusted by the Seal Intensity front panel settings 150 is then utilized by an RF generation system, as described above, and an initial RF sealing pulse is then started.

The Seal Intensity front panel settings, as shown in FIGS. 9B and 9C, represent approximate parametric values of several preferred embodiments, identified as an example to achieve vessel sealing performance in clinical procedures. The variety of tissue types and surgical procedures requires the use of one or more Seal Intensity front panel settings.

Figure 16:
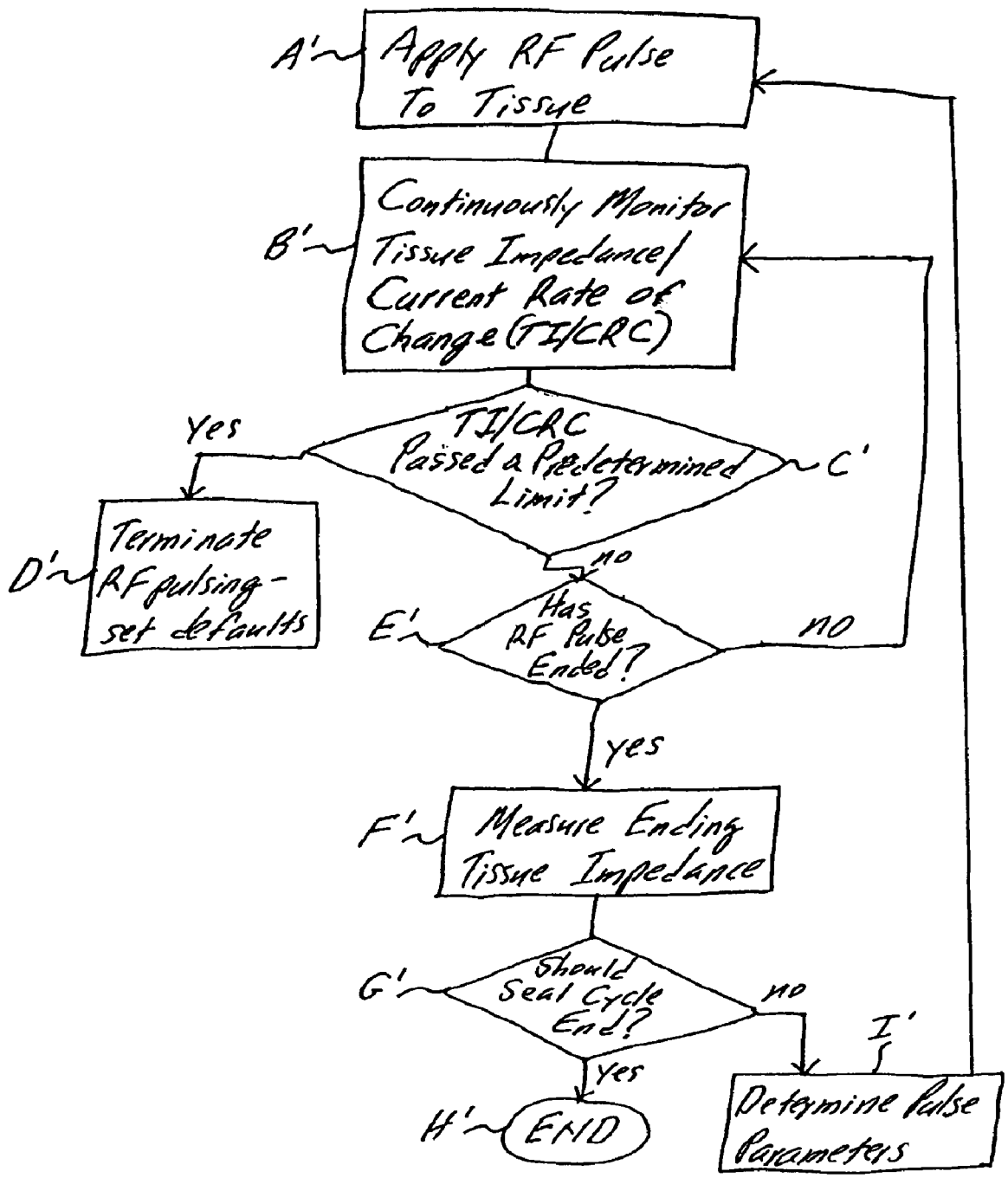
FIG. 16 is a logic flow diagram that illustrates another method in accordance with the system disclosed herein.

FIG. 16 is a logic flow diagram that illustrates a method in accordance with the vessel sealing system. At step A', a RF pulse is applied to tissue. At step B', the current or tissue impedance rate of change is continuously monitored. At step C', a determination is made whether the tissue impedance rate of change has passed a predetermined limit. If yes, at step D', RF pulsing is terminated and any previously changed pulse parameters are reset back to the original defaults. If no, the process proceeds to step E'.

At step E', a determination is made as to whether the RF pulse has ended. If no, the process loops back to step B'. If yes, the process proceeds to step F'. At step F', the ending current or tissue impedance is measured. At step G', the measured ending values are used for determining if the seal cycle should end (based on the current level or ending impedance of the last few RF pulses which did not change by more than a predetermined amount). If yes, the process terminates at step H'. If no, the process continues at step I', where the ending values are used for determining the pulse parameters, i.e., the power, pulse width, current and/or voltage levels, and the duty cycle of the subsequent RF pulse from an entry in one of a plurality of lookup tables. The process then loops back to step A'. One of the plurality of lookup tables is selected manually or automatically, based on a choice of an electrosurgical tool or instrument While the system has been particularly shown and described with respect to preferred embodiments thereof, it will be understood by those skilled in the art that changes in form and details may be made therein without departing from its scope and spirit.

What is claimed is:

1. A method for electrosurgically sealing tissue comprising the steps of:
    providing an electrosurgical generator including an RF energy source and a controller that controls the operation of the electrosurgical generator, the electrosurgical generator having an output which couples to at least one electrode of a surgical instrument;
    instructing the controller to activate the electrosurgical generator to generate an initial pulse of RF energy to tissue to measure a value of an electrical characteristic of the tissue in response to the applied initial pulse;
    determining an initial set of pulse parameters for at least one subsequent pulse based on the initial pulse of RF energy to tissue; and
    controlling the pulse parameters of individual pulses of further subsequent RF energy pulses in accordance with a change in the electrical characteristics of the tissue as determined from at least one characteristic of an electrical transient that occurs during at least one RF energy pulse.

2. A method as in claim 1, wherein the duration of the initial pulse of RF energy is about 100 milliseconds.

3. A method as in claim 1, wherein the value of an electrical characteristic of the tissue is selected from a group consisting of an electric current transient and tissue impedance.

4. A method as in claim 3, wherein the electric current transient is selected from a group consisting of a rate of change of an electric current transient, a rate of change of the tissue impedance, and phase rotation of voltage and current.

5. A method as in claim 1, wherein the initial set of pulse parameters is selected from a group consisting of a magnitude of a starting power, a magnitude of a starting voltage, a magnitude of a starting current, RF power output, current, voltage and pulse width and duty cycle.

6. A method as in claim 1, wherein the change in the electrical characteristics of the tissue is selected from electric current transient and tissue impedance.

7. A method as in claim 6, wherein the electric current transient is selected from a group consisting of a rate of change of an electric current transient, a rate of change of the tissue impedance, and phase rotation of voltage and current.

8. A method as in claim 1, further comprising the step of determining if the tissue responded to the first pulse of RF energy prior to the step of applying at least one subsequent RF energy pulse.

9. A method as in claim 1, further comprising the step of modifying predetermined parameters of the set of RE energy parameters in accordance with a control input from an operator.

10. A method as in claim 1, further comprising the step of terminating generation of at least one of the subsequent RF energy pulses upon a determination that the electrical transient is absent.

11. A method as in claim 1, wherein the step determining an initial set of pulse parameters further includes the step of using the measured value of an electrical characteristic of tissue to readout at least two or more RF energy parameters from an entry in one of a plurality of lookup tables.

12. A method as in claim 11, wherein the RF energy parameters in one of the plurality of lookup tables includes power, start voltage, voltage decay and dwell time.

13. A method as in claim 11, wherein the one of the plurality of lookup tables is selected manually or automatically, based on a choice of an electrosurgical tool or instrument.

14. A method as in claim 1, wherein the at least one characteristic of an electrical transient is selected from a group consisting of electric current transient and tissue impedance.

15. A method as in claim 14, wherein the electric current transient is selected from a group consisting of a rate of change of an electric current transient, a rate of change of the tissue impedance, and phase rotation of voltage and current.

* * * * *